(12) United States Patent
Sato

(10) Patent No.: US 11,304,726 B2
(45) Date of Patent: Apr. 19, 2022

(54) TISSUE-FASTENING TOOL INDWELLING SYSTEM AND METHOD FOR INDWELLING TISSUE-FASTENING TOOL

(71) Applicant: OLYMPUS CORPORATION, Hachioji (JP)

(72) Inventor: Masatoshi Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 399 days.

(21) Appl. No.: 16/668,030

(22) Filed: Oct. 30, 2019

(65) Prior Publication Data
US 2020/0060725 A1 Feb. 27, 2020

Related U.S. Application Data

(63) Continuation of application No. PCT/JP2017/018345, filed on May 16, 2017.

(51) Int. Cl.
*A61B 17/34* (2006.01)
*A61B 17/08* (2006.01)
(Continued)

(52) U.S. Cl.
CPC ........ *A61B 17/3468* (2013.01); *A61B 17/083* (2013.01); *A61B 17/3478* (2013.01);
(Continued)

(58) Field of Classification Search
CPC .... A61B 2017/0649; A61B 2017/0645; A61B 2017/3405; A61B 17/083; A61B 17/068; A61B 17/3468; A61B 17/0644
See application file for complete search history.

(56) References Cited

U.S. PATENT DOCUMENTS

| 2010/0010509 A1 | 1/2010 | Ishioka et al. |
| 2013/0325038 A1* | 12/2013 | Sato ............ A61B 17/068 606/139 |
| 2017/0224352 A1 | 8/2017 | Sato |

FOREIGN PATENT DOCUMENTS

| EP | 2 499 975 A1 | 9/2012 |
| EP | 3400884 A1 | 11/2018 |

(Continued)

OTHER PUBLICATIONS

Aug. 4, 2020 Office Action issued in Japanese Patent Application No. 2019-518632.
(Continued)

*Primary Examiner* — Majid Jamialahmadi
(74) *Attorney, Agent, or Firm* — Oliff PLC

(57) ABSTRACT

A tissue-fastening tool indwelling system includes: a sheath; a needle tube disposed in the sheath; a tissue-fastening tool including a wire having a coil region disposable in the needle tube in a stretched state and restorable to a coil shape with the same winding diameter outside the needle tube; a stylet connected to the wire; and a manipulation part for manipulating the stylet to advance the wire and rotate the sheath in a first direction. In a state where a distal end of the needle tube is proximal of the distal end of the sheath, the manipulation part is designed to operate such that the wire is delivered from the sheath by a length of one winding of the coil region per rotation of the sheath by less than one turn, and the protruding coil region biased to have a diameter larger than the winding diameter.

11 Claims, 28 Drawing Sheets

(51) Int. Cl.
*A61B 17/064* (2006.01)
*A61B 17/00* (2006.01)
(52) U.S. Cl.
CPC ............. *A61B 2017/0046* (2013.01); *A61B 2017/0649* (2013.01); *A61B 2017/3405* (2013.01)

(56) References Cited

FOREIGN PATENT DOCUMENTS

| WO | 02/19923 A1 | 3/2002 |
|---|---|---|
| WO | 2011/055700 A1 | 5/2011 |
| WO | 2013/069436 A1 | 5/2013 |
| WO | 2017/047145 A1 | 3/2017 |
| WO | 2017/047147 A1 | 3/2017 |

OTHER PUBLICATIONS

Aug. 15, 2017 International Search Report issued in International Patent Application No. PCT/JP2017/018345.
Nov. 20, 2020 Extended European Search Report issued in European Patent Application No. 17910128.2.

* cited by examiner

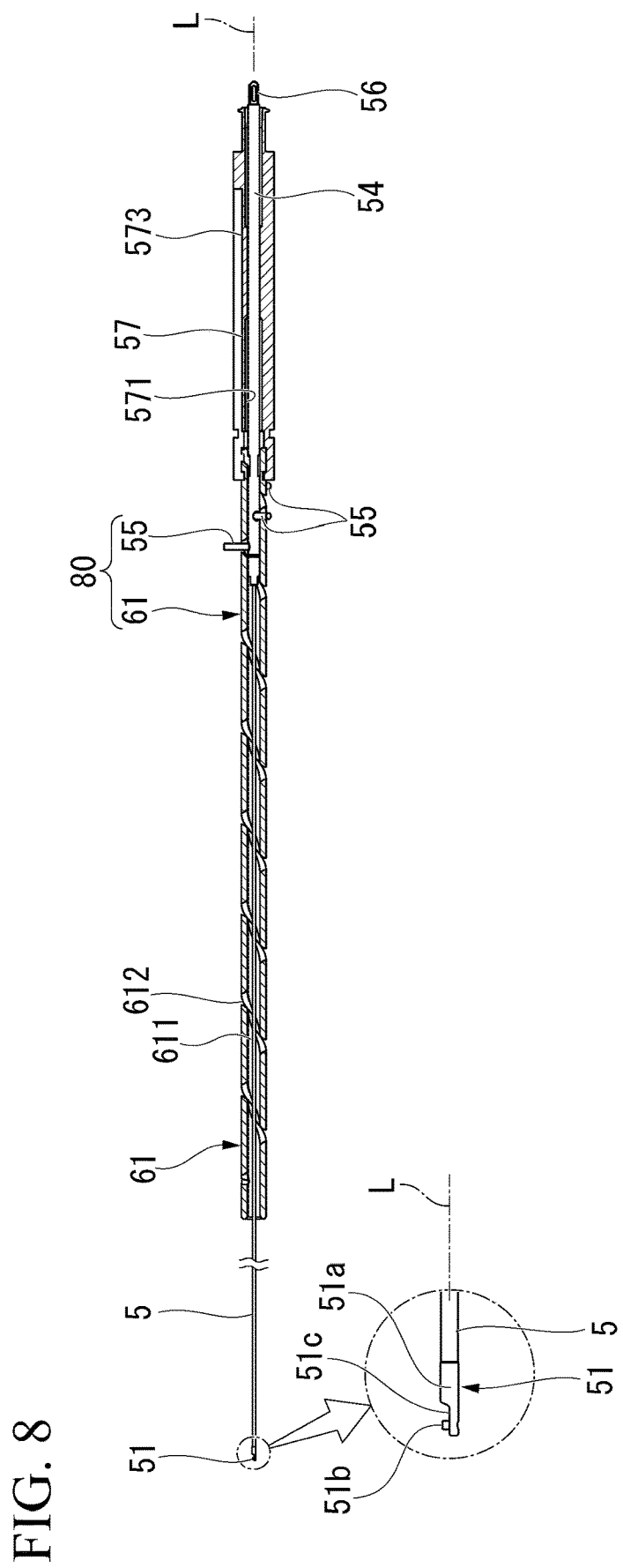

US 11,304,726 B2

TISSUE-FASTENING TOOL INDWELLING SYSTEM AND METHOD FOR INDWELLING TISSUE-FASTENING TOOL

The present disclosure relates to a tissue-fastening tool indwelling system. This application is a continuation application based on PCT Patent Application No. PCT/JP2017/018345, filed May 16, 2017, the content of which is incorporated herein by reference.

BACKGROUND

Past instruments and methods for fastening of tissue in the body include, for example, an instrument for pushing a fastener out of a needle and fastening the fastener to tissue. In the tissue fastening instrument, a stopper for controlling a depth when the needle punctures the tissue and an amount by which the fastener is supplied to the tissue is provided. When a procedure is performed using the tissue fastening instrument, an instrument in which the fastener and the needle are stored pushes onto the tissue. When the needle is advanced and punctures into the tissue, the position of the fastener is fixed by the stopper. Afterwards, the needle is pulled out of the tissue. Since the fastener does not move due to the presence of the stopper, a distal end portion thereof is left behind inside the tissue. When the tissue fastening instrument is removed from the tissue, the rest (the proximal end portion) of the fastener remains outside the tissue. When the fastener is restored to a coil shape, the tissue is fixed.

SUMMARY

The present disclosure is directed to a tissue-fastening tool indwelling system including: a sheath extending from a distal end to a proximal end; a needle tube disposed in the sheath to be projectable and retractable from the distal end of the sheath; a tissue-fastening tool; a stylet connected to an end portion of the tissue-fastening tool; and a manipulation part.

The tissue-fastening tool includes an element wire including a coil region disposable in a stretched state inside the needle tube and restorable to a coil shape with the same winding diameter outside the needle tube.

The manipulation part is designed to manipulate the stylet to advance the tissue-fastening tool and rotate the sheath in a first direction around a longitudinal axis when the stylet is advanced.

In a state in which a distal end of the needle tube is located at a proximal of a distal end of the sheath, the manipulation part is designed to operate such that the tissue-fastening tool is delivered from the sheath by a length of one winding of the coil region per rotation of the sheath in the first direction by an amount of less than one turn, and the coil region of the tissue-fastening tool protruding from the sheath is biased to have a diameter larger than the winding diameter.

A method for indwelling a tissue-fastening tool by a tissue-fastening tool indwelling system includes operating a manipulation part to protrude the tissue-fastening tool disposed inside a needle tube from a distal end of the needle tube by advancing a stylet connected to an end portion of the tissue-fastening tool and disposed inside the needle tube with respect to the needle tube and indwelling a distal end side region of the tissue-fastening tool in a first luminal organ.

The needle tube is disposed in a sheath so as to be projectable and retractable from a distal end of the sheath. The tissue-fastening tool includes an element wire including a coil region that is restorable from a stretched state inside the needle tube to a coil shape in which a plurality of windings have an identical winding diameter when delivered outside the needle tube. When the manipulation tool is operated to advance the stylet, the sheath is rotated in a first direction around a longitudinal axis.

The method further includes pulling the needle tube out of a wall of the first luminal organ and a wall of a second luminal organ while a distal end opening portion of the sheath is brought into contact with the wall of the second luminal organ in a state in which a distal end side region of the coil region of the tissue-fastening tool is indwelled in the first luminal organ and storing the needle tube in the sheath; and indwelling a proximal end side region of the coil region of the tissue-fastening tool in the second luminal organ by deploying the proximal end side region of the coil region of the tissue-fastening tool from the sheath while biasing the proximal end side region to have a diameter larger than the winding diameter.

BRIEF DESCRIPTION OF THE DRAWINGS

FIG. 8 is a cross-sectional view of a stylet and a first cam tube according to the embodiment.

DETAILED DESCRIPTION OF THE PREFERRED EMBODIMENTS

A tissue-fastening tool indwelling system according to an exemplary embodiment (hereinafter simply referred to as an "indwelling system") will be described. The indwelling system includes a tissue-fastening tool indwelled in tissue (hereinafter referred to as an "implant" in some cases) and a tissue-fastening tool indwelling device for indwelling the implant (hereinafter simply referred to as an "indwelling device" in some cases).

Figure 1:
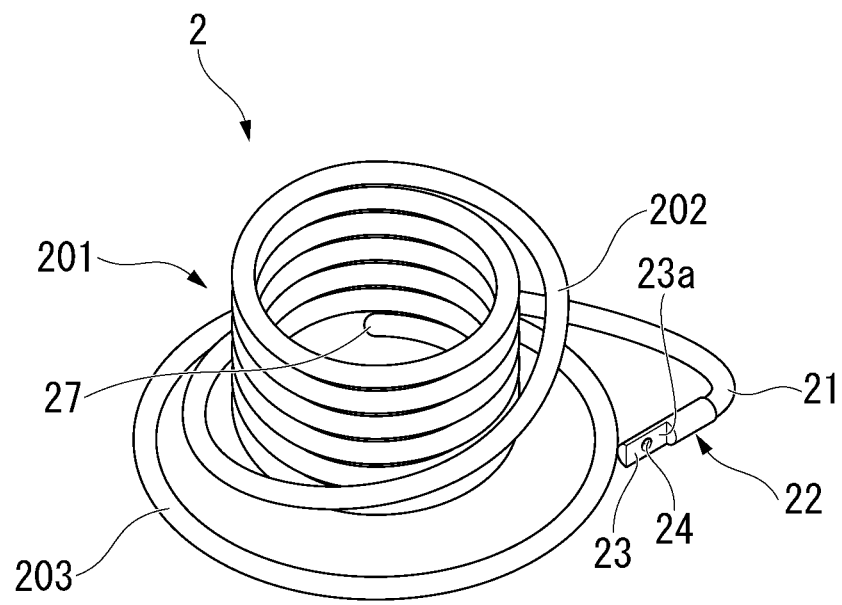
FIG. 1 is a perspective view showing a tissue-fastening tool according to an embodiment.

FIG. 1 is a perspective view of an implant 2. The implant 2 is formed of a single metal element wire and is configured so that the implant 2 can be restored to an indwelling shape (a shape of a tissue-fastening tool 2 at the time of indwelling of the tissue-fastening tool 2) shown in FIG. 1 from a state in which the implant 2 extends substantially linearly. As the metal element wire, an element wire made of a shape memory alloy, a super elastic wire, or the like can be used.

The implant 2 includes a coil region 201 to be indwelled to be fastened tissue therebetween, a helical coupling part 202 connected to a proximal end side of the coil region 201, and an outer circumferential loop 203 connected to a proximal end side of the coupling part 202.

The coil region 201 is formed such that a plurality of windings, which have same winding diameter, of the coil region 201 are lined from a distal end 27 to the proximal end thereof in an indwelling shape. The coupling part 202 extends outward in a radial direction of the coil region 201 and extends helically from the proximal end side thereof toward a distal end thereof. That is to say, a helical diameter of the coupling part 202 is larger than a winding diameter of the coil region 201. The outer circumferential loop 203 is a region including a proximal end 21 of the implant 2 and forms a closed loop to surround the coil region 201.

Figure 2:
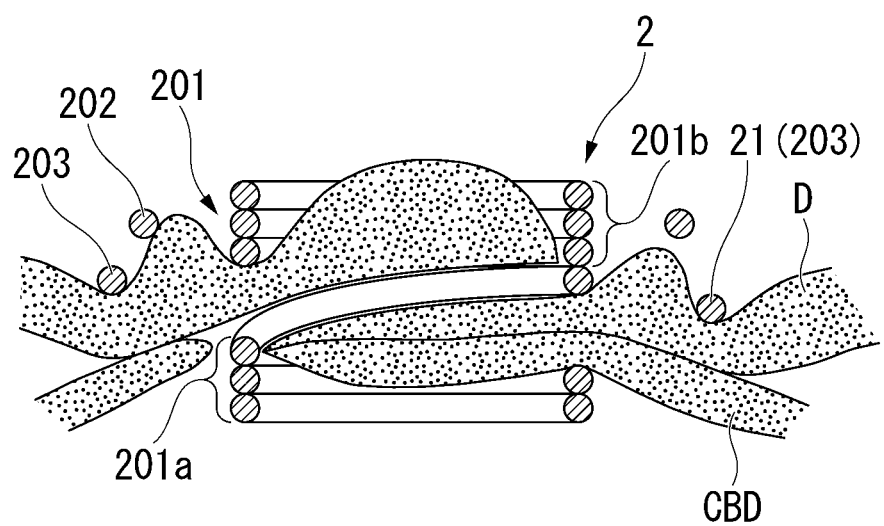
FIG. 2 is a diagram showing an ideal indwelling mode of the tissue-fastening tool.

FIG. 2 shows an ideal indwelling mode of the implant 2. In this example, the implant 2 is disposed so that two luminal tissues, i.e., duodenal tissue D and common bile duct tissue CBD are fastened in the coil region 201. In the ideal indwelling mode, the plurality of windings in the coil region 201 are stacked in order without changing the order and substantially the same number are disposed as a proximal end side region 201b and a distal end side region 201a on a duodenum side and a common bile duct side. Furthermore, a helical shape of the coupling part 202 is also restored in order without being entangled.

When the implant 2 is ideally indwelled, the tissue D and the tissue CBD fastened by the coil region 201 are sufficiently tightened so that a blood flow is blocked. As a result, tissues located at an outer edge of the loop of the coil region 201 adhere. Furthermore, tissues located in the loop of the coil region 201 are necrosed and fall off after a certain period of time. The outer circumferential loop 203 presses the tissue D to be brought into close contact with the tissue CBD by being biased by the coupling part 202 restored in a spring shape, thereby preventing bile or the like flowing in the common bile duct from leaking into the abdominal cavity at a stage before the tissue adheres. At the same time, since the coupling part 202 biases the coil region 201 toward the inside of the tissue D, the implant 2 is removed from an indwelled portion and falls into the duodenum when the tissue located in the loop of the coil region 201 are necrosed and fall off. After the fallen implant 2 is discharged from a digestive tract to the outside of the body, only a hole through which the common bile duct communicates with the duodenum remains and the bile can be discharged from the hole into the duodenum.

The indwelling system according to this embodiment is configured such that the implant 2 is indwelled in the tissue in the above ideal indwelling mode without depending on a user's skill so that the implant 2 can appropriately exhibit the above function. A description will be provided in detail below.

The implant 2 includes an implant-coupling part (a coupling part) 22 at the proximal end 21. As shown in FIG. 1, the implant-coupling part 22 includes a first engagement part main body 23 and a recessed part 24. The first engagement part main body 23 has a semicircular pillar-shaped part obtained by cutting a cylinder in half along a central axis thereof. The recessed part 24 is a hole formed to extend in a perpendicular direction from a planar part 23a parallel to a longitudinal axis of the first engagement part main body 23. The implant-coupling part 22 is configured to be engageable with a stylet to be described later.

Figure 3:
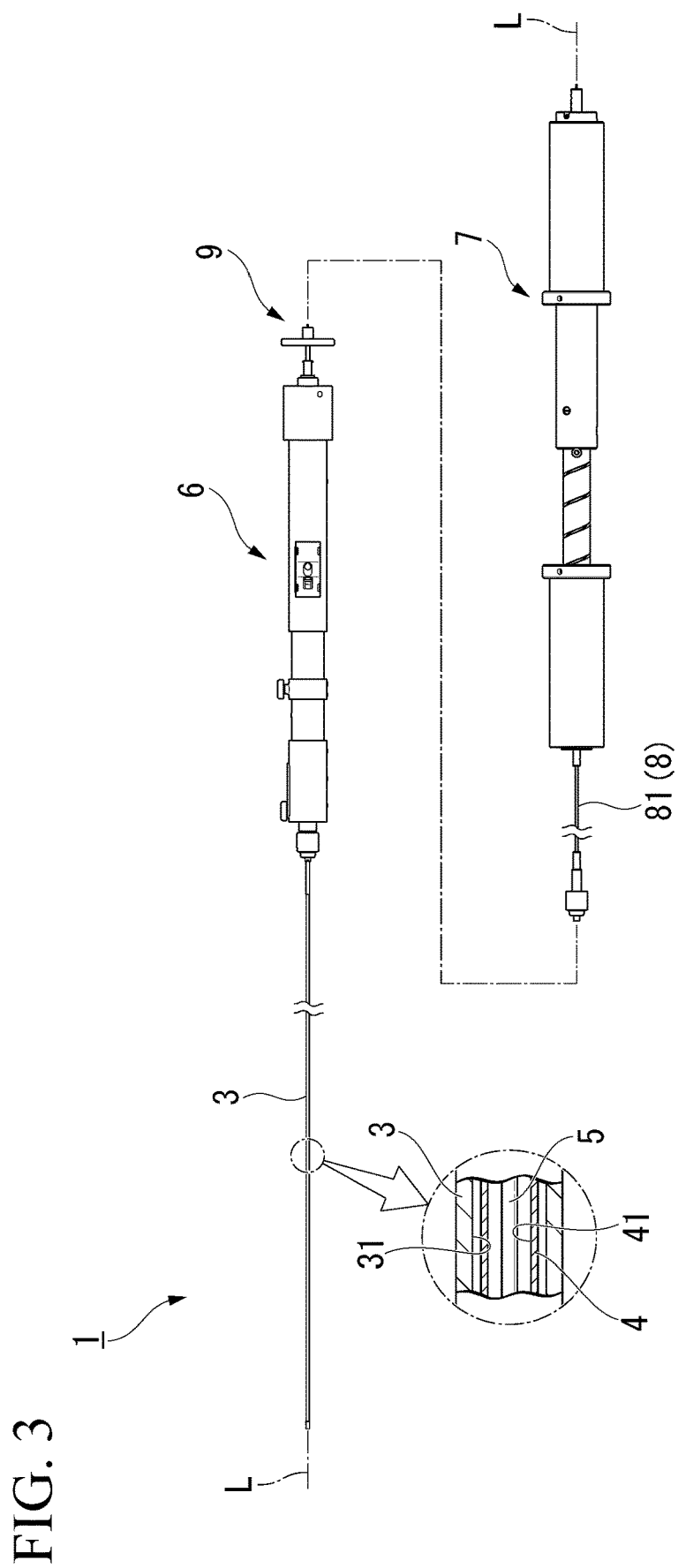
FIG. 3 is an overall diagram showing a tissue-fastening tool indwelling device according to the embodiment.

FIG. 3 is an overall diagram showing an indwelling device 1 according to this embodiment. The indwelling device 1 is a device for indwelling the tissue-fastening tool 2 in a body using an endoscope. The indwelling device 1 includes a sheath 3, a needle tube (an elongated shaft and a treatment part) 4, a stylet (a treatment part) 5, a main manipulation part (a manipulation part) 6, an auxiliary manipulation part (a second manipulation part) 7, and a manipulation transmission member (hereinafter simply referred to as a "transmission member" in some cases) 8. The sheath 3, the needle tube 4, the stylet 5, and the main manipulation part 6 are disposed on a central axis L of the sheath 3. The auxiliary manipulation part 7 is coupled to the main manipulation part 6 on the central axis L of the sheath 3. In the following description of the main manipulation part 6 and the auxiliary manipulation part 7, a "central axis" is used with a meaning including an extension line of the central axis L of the sheath 3 when the main manipulation part 6 and the auxiliary manipulation part 7 are disposed on the central axis L of the sheath 3.

A lumen 31 which extends from a distal end thereof to a proximal end thereof is formed inside the sheath 3 and the needle tube 4 is disposed in the lumen 31 so as to freely advance and retract.

The proximal end side of the sheath 3 is connected to the main manipulation part 6. The sheath 3 is inserted into a treatment tool channel 102 of an endoscope insertion part 101 (refer to FIG. 21).

Figure 4:
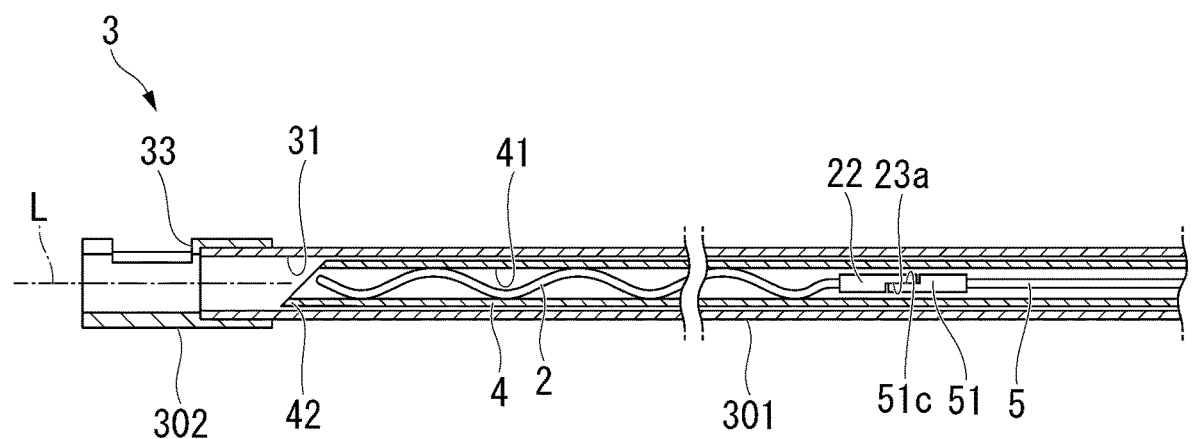
FIG. 4 is a cross-sectional view showing a distal end portion of a tissue-fastening tool indwelling device.

FIG. 4 is a cross-sectional view of the distal end portion of the sheath 3. As shown in FIG. 4, the sheath 3 includes a coil sheath part 301 and a tubular member 302 attached to a distal end portion of the coil sheath part 301. An inner diameter of the tubular member 302 constituting the distal end portion of the sheath 3 is larger than an inner diameter of the coil sheath part 301.

Figure 5:
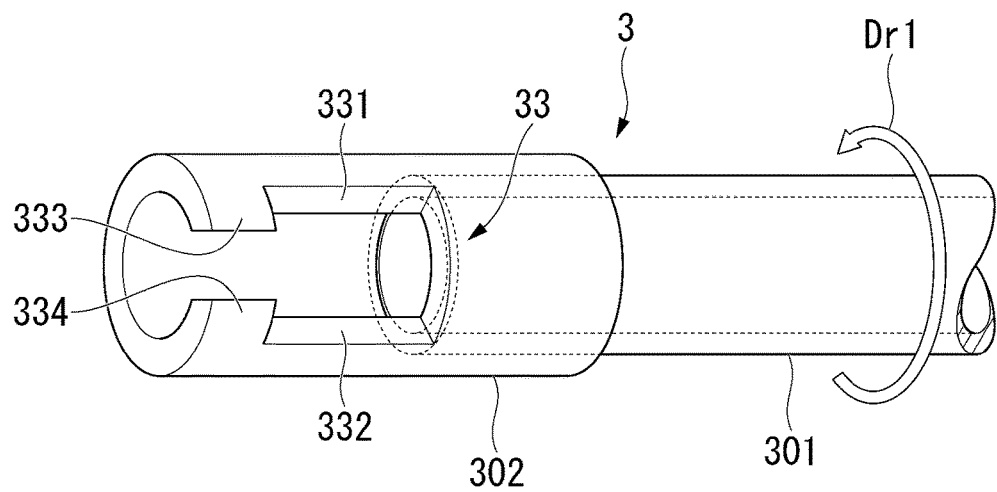
FIG. 5 is a diagram showing a shape of a slit formed at a distal end portion of a sheath.

A slit 33 extend substantially parallel to the central axis L from a distal end toward a proximal side of the tubular member 302 is formed by hollowing a part of an outer circumstantial surface of the tubular member 302. FIG. 5 is a diagram showing a shape of the slit 33. As shown in FIG. 5, a circumferential edge of the slit 33 has a pair of regions, i.e., a first circumferential edge 331 and a second circumferential edge 332 which face each other in a circumferential direction of the sheath 3. The slit 33 communicates with a distal end opening of the sheath 3. When a rotational direction of the sheath 3 at the time of indwelling the implant 2, that is, a direction in which the sheath 3 rotates when the stylet 5 advances is defined as a rotational direction (first direction) Dr1, the first circumferential edge 331 is located on a downstream side in the rotational direction Dr1. The second circumferential edge 332 is located on an upstream side in the rotational direction Dr1.

From a region of the first circumferential edge 331 located on the distal end side of the sheath 3, a protrusion 333 protrudes in a direction of the second circumferential edge 332, that is, in an upstream direction in the rotational direction Dr1. From a region of the second circumferential edge 332 located on the distal end side of the sheath 3, the second protrusion 334 protrudes in a direction of the first circumferential edge 331, that is, in a downstream direction of the rotational direction Dr1. That is to say, the protrusion 333 and the second protrusion 334 protrude to face each other. A width dimension of the slit 33 is reduced only on the distal end side of the sheath 3 due to the existence of the protrusion 333 and the second protrusion 334. A slit width of a portion having the protrusion 333 and the second protrusion 334 provided therein is larger than a diameter of the metal element wire of the implant 2. Therefore, the metal element wire is capable of passing into and out of the slit 33 between the protrusion 333 and the second protrusion 334.

As shown in FIG. 4, the needle tube 4 is a long member having a hollow needle tube insertion passage (an insertion passage) 41. The needle tube 4 is inserted into the lumen 31 to be projectable and retractable from the distal end of the sheath 3. A distal end (a puncturing part and a needle tip) 42 of the needle tube 4 is formed to be sharp and functions as a puncture needle. A proximal end of the needle tube 4 is attached to a distal end of a needle guide 67 (refer to FIG. 7A), which will be described later, to be relatively rotatable and immovable forward and backward. That is to say, the needle guide 67 freely rotates around the central axis L with respect to the needle tube 4 and fixed in a central axial direction with respect to the needle tube. A superelastic alloy represented by a nickel titanium alloy or stainless steel can be adopted, for example, as a material of the needle tube 4.

The stylet 5 is a long core material, a distal end portion thereof is located in the needle tube insertion passage 41 (refer to FIG. 3), and a proximal end portion thereof extends to the main manipulation part 6 provided on the proximal end side of the sheath 3. The stylet 5 is a member which advances and retracts the tissue-fastening tool 2 with respect to the needle tube insertion passage 41. The stylet 5 is configured to be projectable and retractable from the distal end of the sheath 3.

FIG. 8 is a cross-sectional view of the stylet 5 and a first cam tube (a cam tube) 61. As shown in FIG. 8, a distal end engagement part 51 is provided at a distal end portion of the stylet 5. The distal end engagement part 51 includes a second engagement part main body 51a and a protruding part 51b. A proximal end portion of the second engagement part main body 51a has a cylindrical shape and a distal end portion thereof has a semi-cylindrical shape obtained by cutting a cylinder in half on the central axis L. The protruding part 51b is formed to protrude in a perpendicular direction from the planar part 51c of the second engagement part main body 51a parallel to the central axis L. As shown in FIG. 4, when the planar parts 23a and 51c come into contact with each other in the needle tube 4 and the protruding part 51b is inserted into the recessed part 24, the distal end engagement part 51 and the implant-coupling part (a proximal end portion of the tissue-fastening tool 2) 22 engage with each other and the tissue-fastening tool 2 is coupled to the stylet 5.

As shown in FIG. 8, a stylet proximal end member 54 is fixed to a proximal end portion of the stylet 5. Three first engaging pins (cam followers, first projections, and a guided part) 55 are provided at a distal end portion of the stylet proximal end member 54 to protrude in an orthogonal direction (outward in a radial direction) with respect to the central axis L from an outer circumstantial surface thereof. The three first engaging pins 55 are each provided to be spaced apart at an equal angle in a circumferential direction and spaced apart at an equal interval in the direction of the central axis L.

Figure 7A:
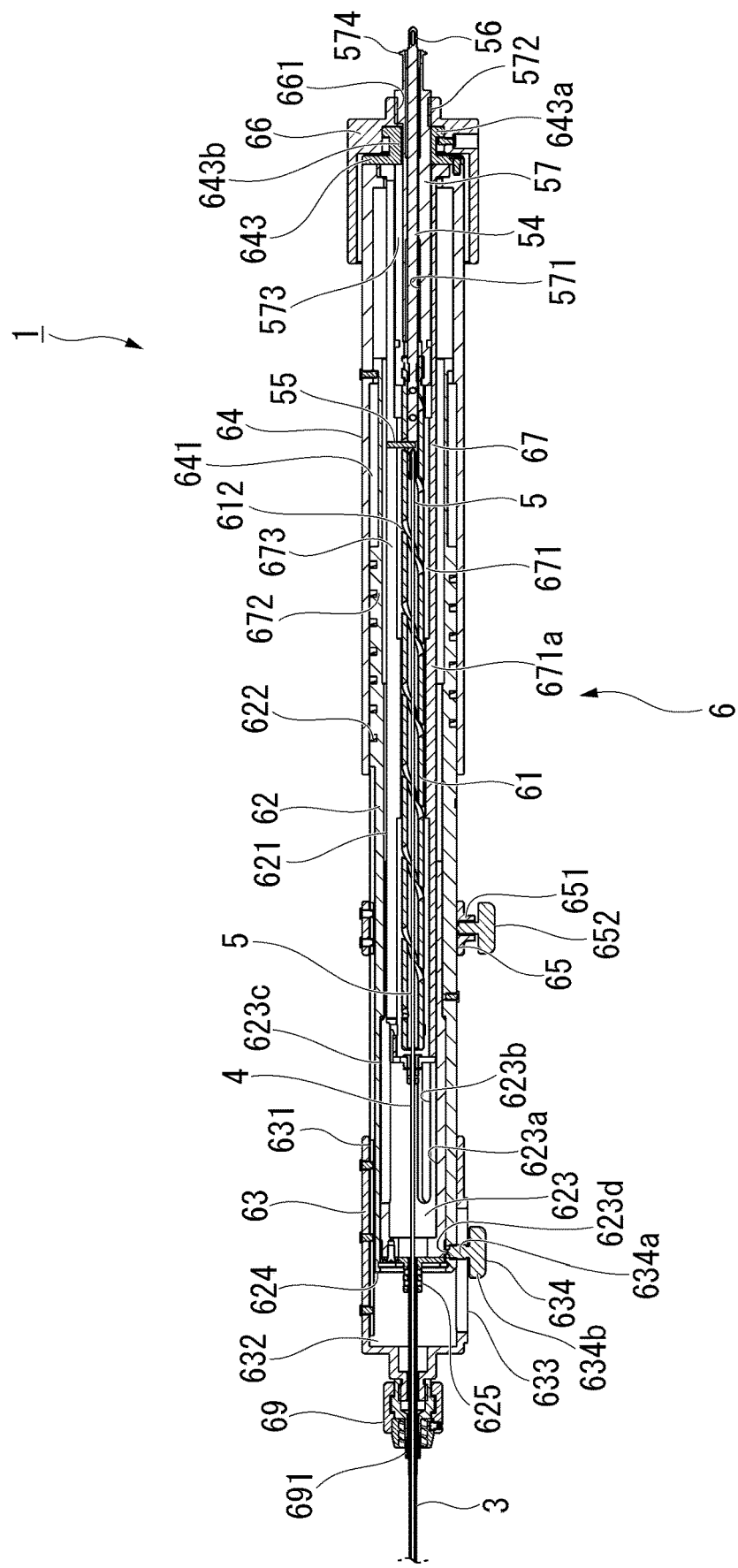
FIG. 7A is a cross-sectional view of the main manipulation part according to the embodiment.
Figure 7B:
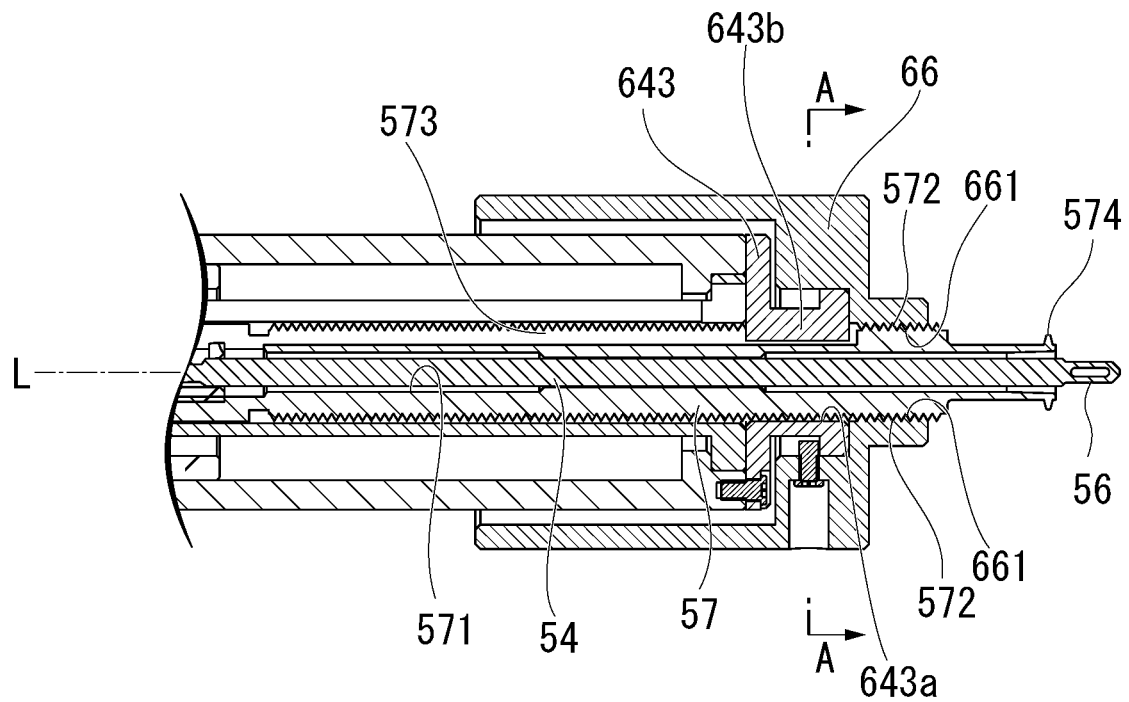
FIG. 7B is a cross-sectional view of a proximal end portion of the main manipulation part according to the embodiment.
Figure 7C:
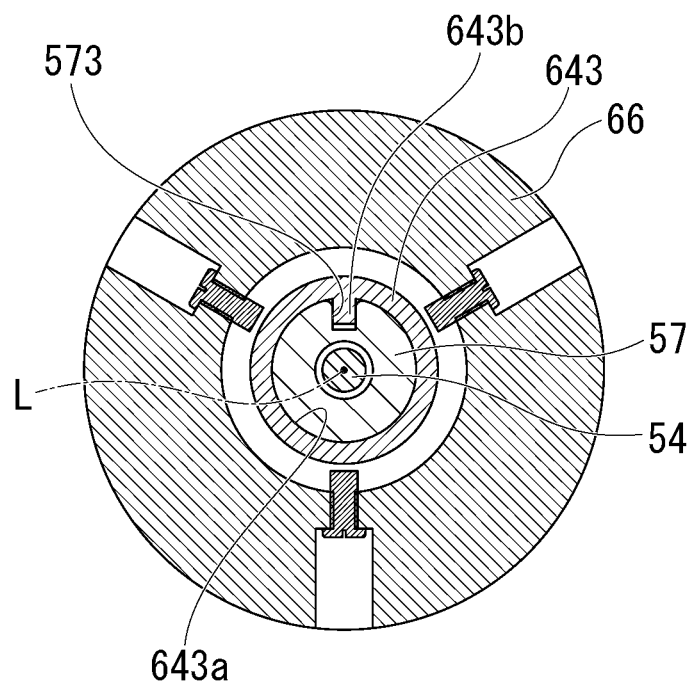
FIG. 7C is a cross-sectional view taken along line A-A in FIG. 7B.
Figure 9:
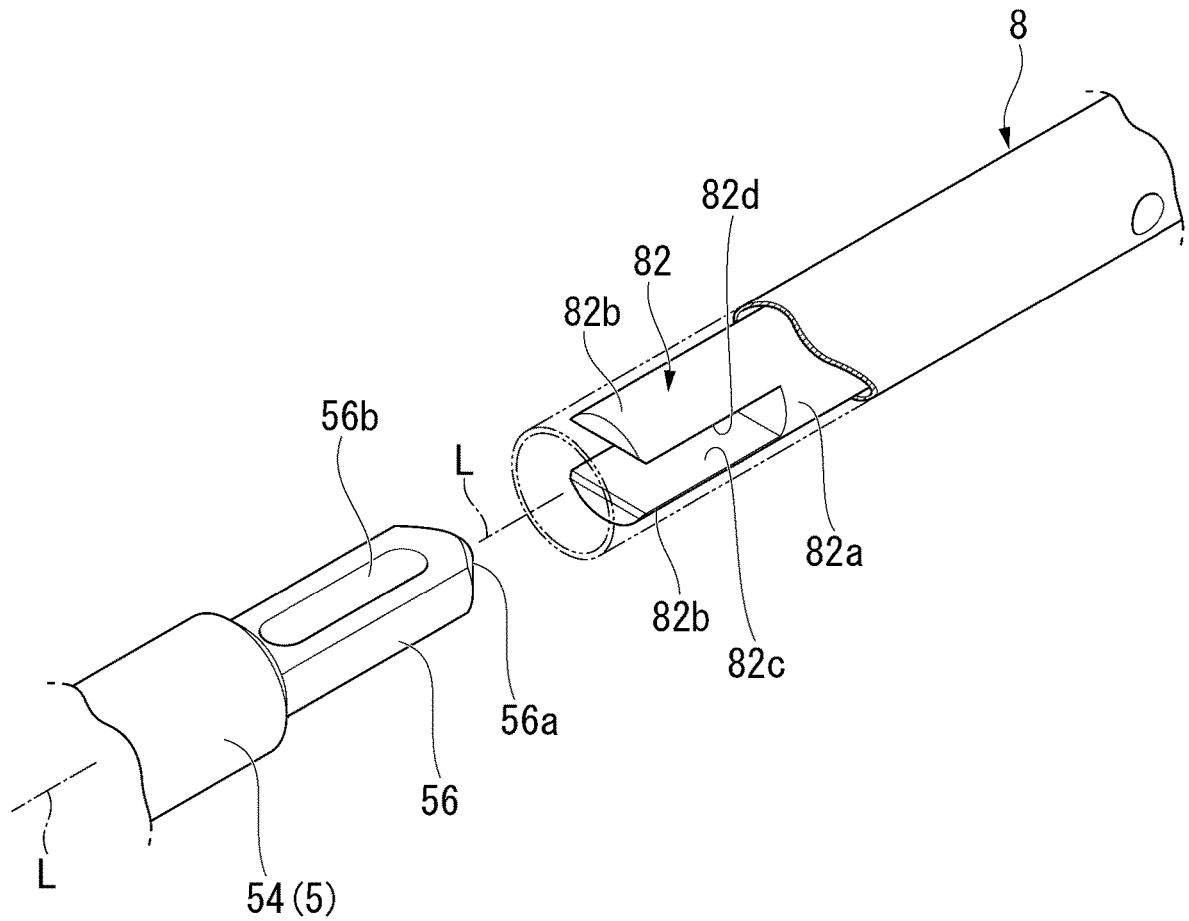
FIG. 9 is a perspective view of a proximal end portion of the stylet and a distal end portion of the manipulation transmission member according to the embodiment.

As shown in FIGS. 7A, 7B, and 8, the stylet proximal end member 54 is inserted through a lumen 571 of a Luer joint (an intermediate member) 57. FIG. 9 is a perspective view of the proximal end portion (a stylet proximal end member 54) of the stylet 5 and a distal end portion of a transmission member 8. A proximal end engagement part 56 is provided on the stylet proximal end member 54. The proximal end engagement part 56 is an engagement member which engages with the distal end portion of the transmission member 8. As shown in FIG. 9, the proximal end engagement part 56 has a substantially flat plate shape and is provided to extend along the central axis L from a proximal end of the stylet proximal end member 54. A proximal end portion 56a of the proximal end engagement part 56 has a surface which protrudes toward a proximal end side. A through hole 56b is formed in the proximal end engagement part 56. The proximal end engagement part 56 has a size such that the proximal end engagement part 56 is located further inward than a maximum outer diameter part of the stylet 5 when viewed from the direction of the central axis L.

As shown in FIG. 4, the stylet 5 and the needle tube 4 are inserted through the lumen 31 of the sheath 3 so as to be coaxial with the central axis L of the sheath 3. The sheath 3, the needle tube 4, and the stylet 5 are members which are inserted into a body from a distal end side and are made of materials which are elastically deformable along with bending of the treatment tool channel 102 when inserted through the treatment tool channel 102 of an endoscope 100.

Figure 6:
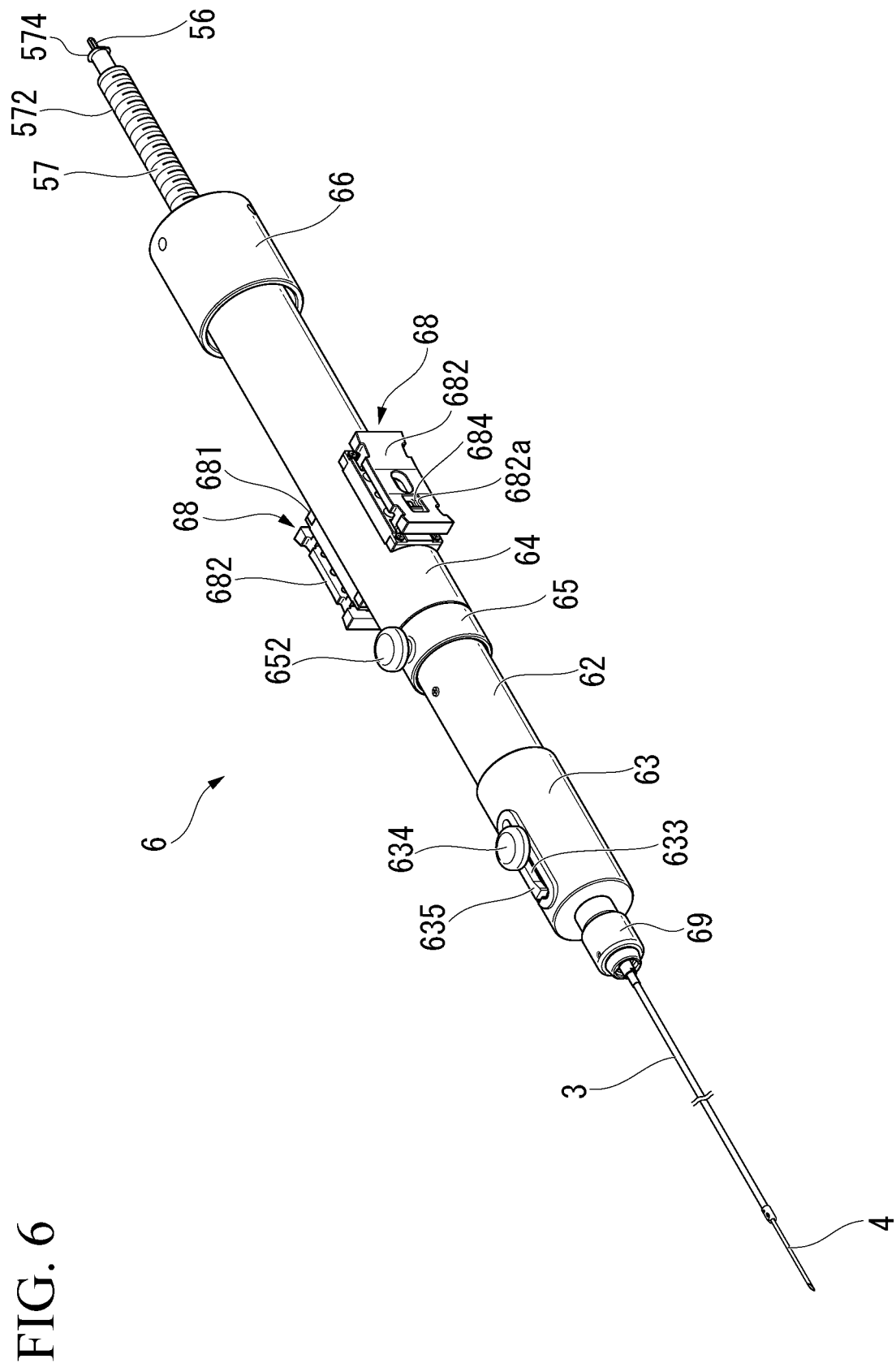
FIG. 6 is a perspective view of a main manipulation part according to the embodiment.

The main manipulation part 6 is provided along the central axis L of the sheath 3 on the proximal end side of the sheath 3. FIG. 6 is a perspective view of the main manipulation part 6. FIG. 7A is a cross-sectional view of the main manipulation part 6. FIG. 7B is a cross-sectional view of a proximal end portion of the main manipulation part 6. FIG. 3 shows the main manipulation part 6 in a state in which a jig 9 to be described later is installed therein and FIGS. 6, 7A, 7B, and 7C show the main manipulation part 6 from which the jig 9 is removed. The main manipulation part 6 is provided to operate the sheath 3, the needle tube 4, and the stylet 5. The main manipulation part 6 includes the first cam tube 61, a main manipulation part main body 62, a sheath slider 63, a needle slider (a slider part or an elongated shaft manipulation part) 64, a needle slider stopper 65, a first rotation knob (an elongated shaft manipulation part and a first manipulation input part) 66, the needle guide (a guide part) 67, and a mounting part 69.

As shown in FIG. 8, the first cam tube 61 is a tube in which a first insertion passage 611 extending along the central axis L and a first guide passage (a cam, a guide passage, and a first helical groove) 612 are formed. The proximal end portion of the stylet 5 is inserted through the first cam tube 61. The first guide passage 612 communicates with an inside and outside of the tube and is formed in a helical shape. The helical shape of the first guide passage 612 is formed such that the first engaging pin 55 advances from a proximal end of the first guide passage 612 toward a distal end thereof while rotating right when viewed from the proximal end toward the distal end.

Figure 10:
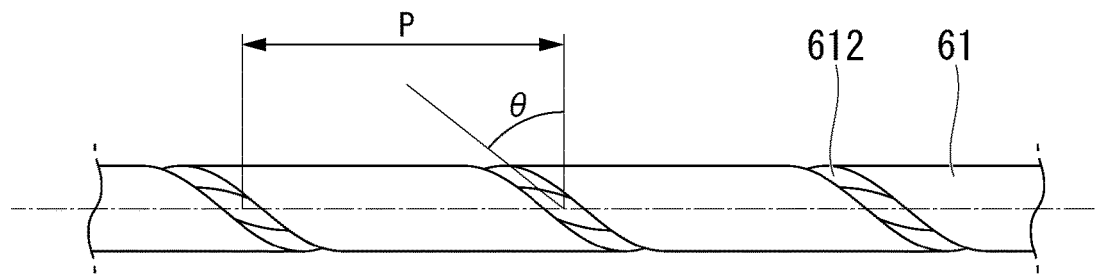
FIG. 10 is a schematic view showing a first guide passage of the first cam tube according to the embodiment.

FIG. 10 is a schematic view showing the helical shape of the first guide passage 612. As shown in FIG. 10, the helical shape of the first guide passage 612 is formed at a constant pitch. A helical pitch P of the helical shape of the first guide passage 612 is set so that the sheath 3 rotates by less than one turn while a metal element wire of the proximal end side region 201b of the coil region 201 in the tissue-fastening tool 2 indwelled in a luminal organ on a proximal side is delivered for one turn. Furthermore, at the same time, the helical pitch P is set so that the sheath 3 rotates more than one turn while the metal element wires constituting the coupling part 202 and the outer circumferential loop 203 are delivered for one turn.

The number of helical turns (the number of turns) in the helical shape of the first guide passage 612 can be appropriately set in consideration of the number of turns and the like of the proximal end side region 201b in an indwelling shape of the tissue-fastening tool 2 within a range in which the helical pitch P satisfies the above-described conditions. In this embodiment, the helical pitch P is longer than the length of one winding of the coil region 201 and shorter than any one of the length of one turn of the coupling part 202 and the length of one winding of the outer circumferential loop 203.

Also, the first guide passage 612 is set to a range in which a lead angle θ is 20 degrees or more and 75 degrees or less.

As shown in FIGS. 7A and 8, the stylet 5 and the stylet proximal end member 54 are inserted into the first cam tube 61. The first cam tube 61 and the three first engaging pins 55 of the stylet proximal end member 54 constitute a first helical mechanism 80. The first engaging pins 55 are slidably engaged in the first guide passage 612 of the first cam tube 61. Furthermore, the three first engaging pins 55 of the stylet proximal end member 54 are inserted into the first guide passage 612 to protrude outward from the first insertion passage 611. By the engagement between the three first engaging pins 55 and the first guide passage 612, the stylet 5 and the stylet proximal end member 54 are configured to be supported by the first cam tube 61 and to advance and retract while rotating with respect to the first cam tube 61. In this way, the helical mechanism defines the motion of the stylet 5.

A proximal end side of the first cam tube 61 and a distal end side of the Luer joint 57 are fixed to each other. The Luer joint 57 and the stylet 5 are configured to be relatively rotatable. The stylet 5 and the stylet proximal end member 54 can advance and retract in the direction of the central axis L while rotating with respect to the first cam tube 61 and the Luer joint 57.

Figure 7D:
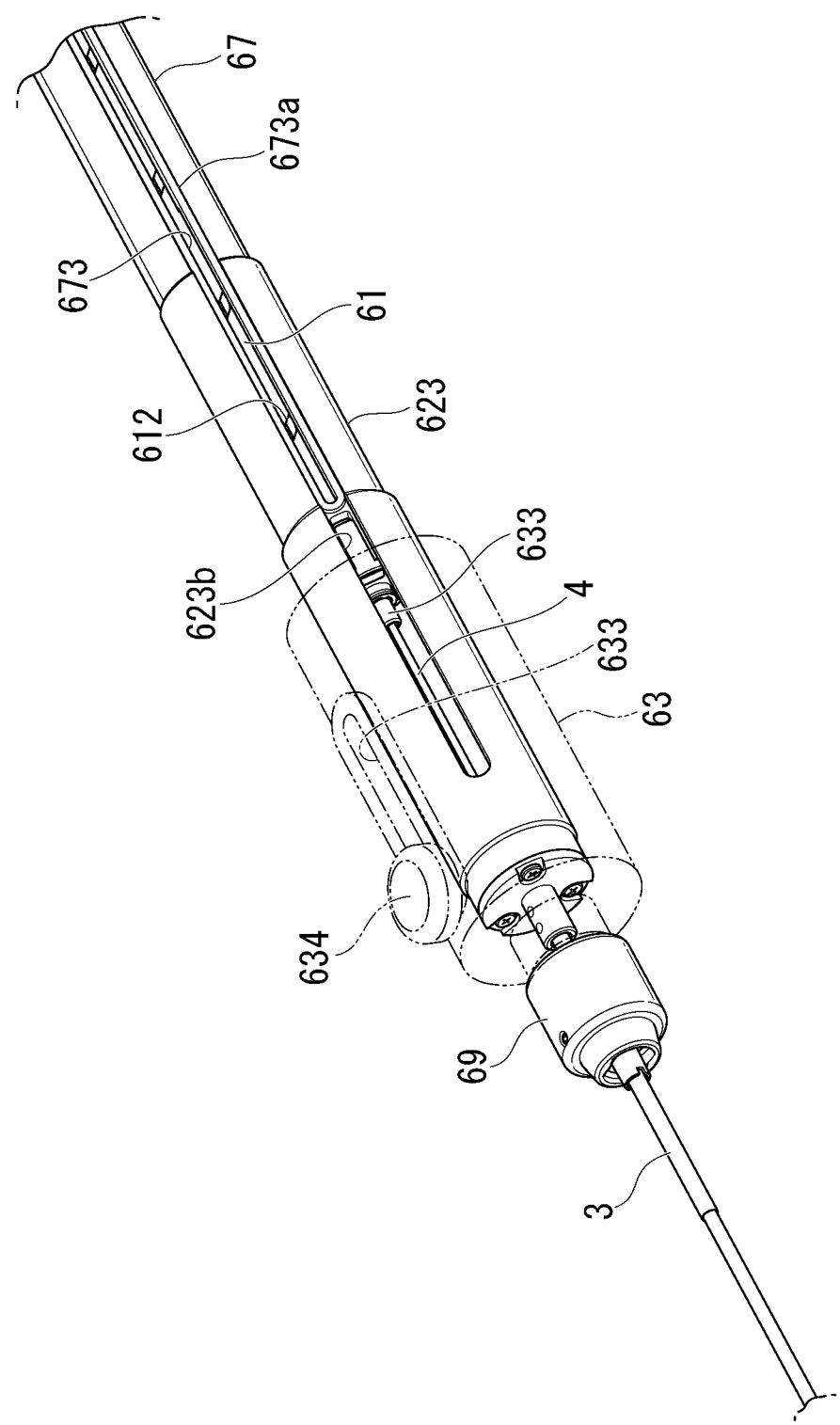
FIG. 7D is a perspective view showing a state in which a needle guide is inserted into a sheath guide according to the embodiment.
Figure 11:
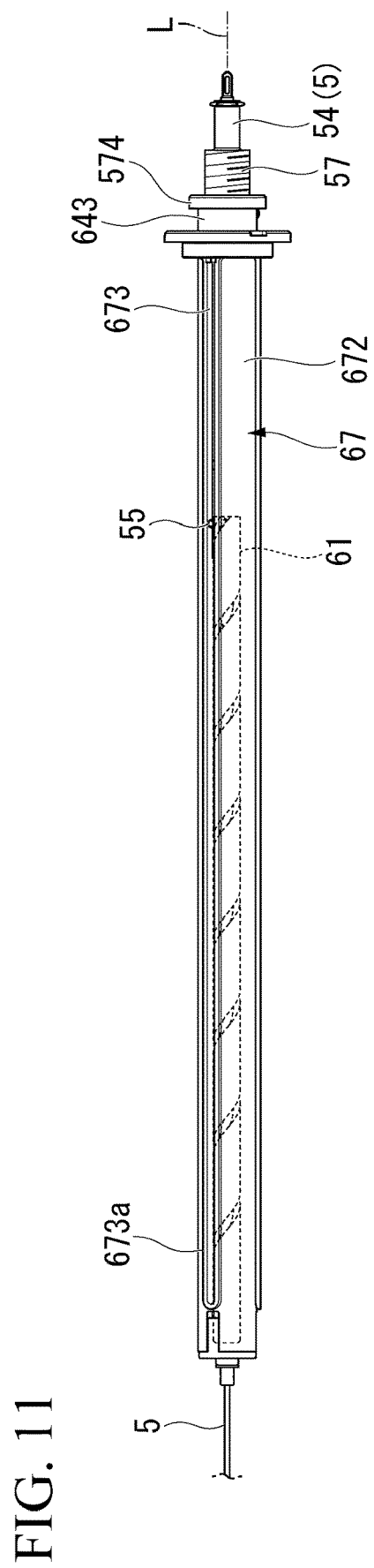
FIG. 11 is a side view showing a state in which the stylet and a stylet proximal end member are inserted into the needle guide according to the embodiment.

As shown in FIG. 11, the needle guide 67 has a substantially cylindrical shape, and as shown in FIG. 7A, includes a needle guide insertion passage 671 which extends in the direction of the central axis L. As shown in FIGS. 7D and 11, on a side wall part 672 of the needle guide 67, a slit surface which forms guide slits 673 communicating an outside of the needle guide 67 with an inside of the needle guide insertion passage 671 is straightly formed in the direction of the central axis L. The three guide slits 673 are formed at equal intervals in a circumferential direction of the needle guide 67.

As shown in FIG. 7A, the needle guide insertion passage 671 is formed with a small-diameter part 671a having a small opening diameter of the needle guide insertion passage 671 in a partial region in the direction of the central axis L. The opening diameter of the small-diameter part 671a is set to be slightly larger than an outer diameter of the first cam tube 61.

A needle slider end member 643 is fixed to a proximal end of the needle slider 64. The needle guide 67 is sandwiched between the needle slider 64 and the needle slider end member 643 at a proximal end portion and is supported to be capable of only rotating with respect to the needle slider 64.

The stylet 5, the stylet proximal end member 54, the first cam tube 61, and the Luer joint 57 are inserted into the needle guide insertion passage 671 to be advanceable and retractable with respect to the needle guide 67. When the first cam tube 61 is inserted through the small-diameter part 671a of the needle guide 67, the first cam tube 61 is supported to be relatively advanceable, retractable, and rotatable on the central axis L in the needle guide insertion passage 671.

As shown in FIG. 11, the three first engaging pins 55 of the stylet proximal end member 54 are respectively engaged with the guide slits 673 one by one. The first engaging pins 55 is slidable in the guide slit 673. That is to say, the first engaging pins 55 is slidable in the first guide passage 612 and in the guide slit 673.

The first cam tube 61 is supported to be capable of only advancing and retracting with respect to the needle slider 64. The first engaging pins 55 of the stylet proximal end member 54 are engaged with both the first guide passage 612 and the guide slit 673. When the stylet 5 and the stylet proximal end member 54 rotate around the central axis L, the stylet 5 and the stylet proximal end member 54 advance and retract with respect to the needle slider 64 while rotating and the needle guide 67 is configured to only rotate with the stylet 5 and the stylet proximal end member 54. It should be noted that, in this description, a motion in which the stylet 5 advances while rotating is referred to as a "helical motion" in some cases.

As shown in FIGS. 6 and 7A, the main manipulation part main body 62 has a substantially cylindrical shape and includes the second insertion passage 621 extending in the direction of the central axis L formed therein. A sheath guide 623 is inserted into a distal end side of the second insertion passage 621. The needle guide 67 is inserted into a proximal end side of the second insertion passage 621. The sheath guide 623 is rotatably supported with respect to the main manipulation part main body 62 near a distal end of the second insertion passage 621. A sheath fixing part 625 is fixed to a distal end side of the sheath guide 623 and has the proximal end of the sheath 3 fixed thereto.

The sheath guide 623 is a substantially cylindrical member extending in the direction of the central axis L as shown in FIG. 7D and has a third insertion passage 623a formed therein as shown in FIG. 7A. The stylet 5 inserted through the needle guide 67 and the first cam tube 61 is inserted through the third insertion passage 623a to be advanceable and retractable. In the sheath guide 623, three first slits 623b straightly extending in the direction of the central axis L are formed at equal intervals in the circumferential direction. The first slits 623b are engaged with ribs 673a (refer to FIG. 11) formed on a radial outside of the needle guide 67 in the periphery of the guide slit 673. Therefore, when the needle guide 67 rotates about the central axis L, the sheath guide 623 rotates to follow the rotation due to a rotational torque transmitted from the needle guide 67. However, even if the needle guide 67 advances and retracts in the direction of the central axis L, the sheath guide 623 does not follow the movement. From the above, the first helical mechanism 80 rotates the sheath 3 around the central axis L due to the engagement between the cam and each of the cam followers.

The ring-shaped needle slider stopper 65 is externally installed on the main manipulation part main body 62. The needle slider stopper 65 has an inner diameter in which the needle slider stopper 65 is advanceable and retractable in the direction of the central axis L with respect to the main manipulation part main body 62. A screw hole 651 is formed in the needle slider stopper 65. A needle stopper screw 652 is screwed into the screw hole 651. When the needle stopper screw 652 is inserted and screwed into the screw hole 651, a distal end of the needle stopper screw 652 presses an outer circumstantial surface of the main manipulation part main body 62 and a position of the needle slider stopper 65 with respect to the main manipulation part main body 62 is fixed.

Figure 12:
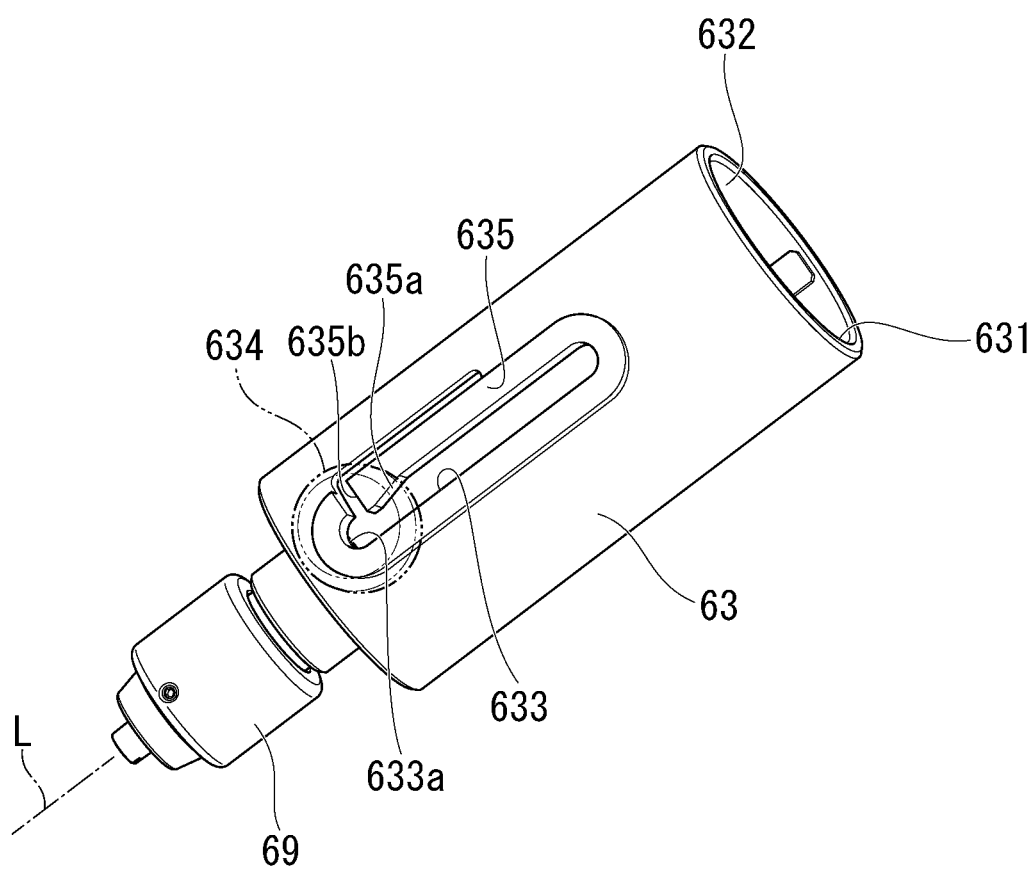
FIG. 12 is a perspective view of the sheath slider according to the embodiment.

The sheath slider 63 is provided on a distal end side of the main manipulation part main body 62. As shown in FIGS. 6 and 12, the sheath slider 63 is a cylindrical member and has a fourth insertion passage 632 extending in the direction of the central axis L from a proximal end opening 631 formed therein. A distal end portion of the main manipulation part main body 62 is inserted through the proximal end opening 631. The main manipulation part main body 62 is provided to be advanceable and retractable in the fourth insertion passage 632.

The mounting part 69 is fixed to a distal end of the sheath slider 63. The mounting part 69 is fixed to a manipulation part 104 of the endoscope 100 by being screw-engaged with a port 103 of the treatment tool channel 102 of the endoscope 100 (refer to FIG. 20). The main manipulation part 6 is fixed to the endoscope 100 by the mounting part 69. A distal end insertion passage 691 extending in the direction of the central axis L is formed in the mounting part 69. The sheath 3 is inserted through the distal end insertion passage 691 to be advanceable and retractable. The sheath 3 can be advanced and retracted by moving the main manipulation part main body 62 to advance and retract in a linear direction with respect to the sheath slider 63.

A second slit 633 extending in the direction of the central axis L is formed in the sheath slider 63. A fixing knob 634 is inserted into the second slit 633 from an outer circumference side thereof. A screw part 634a of the fixing knob 634 passes through the second slit 633 and protrudes toward the fourth insertion passage 632 side of the sheath slider 63. A distal end of the screw part 634a of the fixing knob 634 is inserted into a screw hole 623d formed in an outer circumference of the distal end portion of the main manipulation part main body 62. The length of the screw part 634a is set such that a screw head 634b of the fixing knob 634 can be provided to be spaced apart slightly from the second slit 633 while maintaining a state in which a part of a distal end side of the screw part 634a is screwed into the screw hole of the main manipulation part main body 62.

When the screw part 634a is screwed into the main manipulation part main body 62 side, the sheath slider 63 around the second slit 633 is sandwiched between the screw head 634b and the main manipulation part main body 62. As a result, the positional relationship between the sheath slider 63 and the main manipulation part main body 62 in the direction of the central axis L is fixed. When screwing of the screw part 634a is loosened, the main manipulation part main body 62 is in a state in which the main manipulation part main body 62 can advance and retract in a linear direction with respect to the sheath slider 63. That is to say, relative positions of the main manipulation part main body 62 to the sheath slider 63 can be switched into a fixed state or a relatively movable state due to the second slit 633 and the fixing knob 634.

Depending on a position of the fixing knob 634 with respect to the second slit 633, an amount of protrusion of the sheath 3 from the main manipulation part 6 (an amount of protrusion from the mounting part 69) is determined. The length of the second slit 633 in the direction of the central axis corresponds to an advancement and retraction movement length of the sheath 3. When the fixing knob 634 is disposed at a position at which the fixing knob 634 comes into contact with a distal end of the second slit 633, the amount of protrusion of the sheath 3 from the distal end of the main manipulation part 6 (the amount of protrusion form the mounting part 69) is maximized. On the other hand, when the fixing knob 634 is disposed at a position at which the fixing knob 634 comes into contact with a proximal end of the second slit 633, the sheath 3 is disposed at a maximally retracted position and the amount of protrusion of the sheath 3 from the distal end of the main manipulation part 6 is minimized.

As shown in FIGS. 6 and 12, a resin spring 635 constituted of a cantilever extending in the direction of the central axis L is provided in a part of the second slit 633 of the sheath slider 63. As shown in FIG. 12, an inclined surface 635a and a locking surface 635b are provided on the resin spring 635. When the fixing knob 634 is advanced to a distal end side in the direction of the central axis L, the screw part 634a comes into contact with the inclined surface 635a, advances while gradually pressing the resin spring 635, and comes into contact with the distal end 633a of the second slit 633. The screw part 634a is disengaged from the inclined surface 635a when coming into contact with the distal end 633a of the second slit 633 and the resin spring 635 returns to an original position thereof. Even if a force returning the fixing knob 634 to a proximal end side in the direction of the central axis L acts in this state, the screw part 634a does not return because the screw part 634a comes into contact with the locking surface 635b. From the above, even if the screw part 634a is not screwed into the main manipulation part main body 62, the sheath slider 63 can be fixed while the amount of protrusion of the sheath 3 from the main manipulation part 6 is maximized.

As shown in FIGS. 6 and 7A, the needle slider 64 has a substantially cylindrical shape and is provided along the central axis L in an intermediate part of the main manipulation part 6 in the direction of the central axis L. In a fifth insertion passage 641 formed in the needle slider 64, the stylet 5, the first cam tube 61, the needle guide 67, and the main manipulation part main body 62 are sequentially coaxially disposed from the central axis L side outward in the radial direction. The first rotation knob (the rotation knob) 66, which will be described later, is disposed at a proximal end portion of the needle slider 64.

Figure 13A:
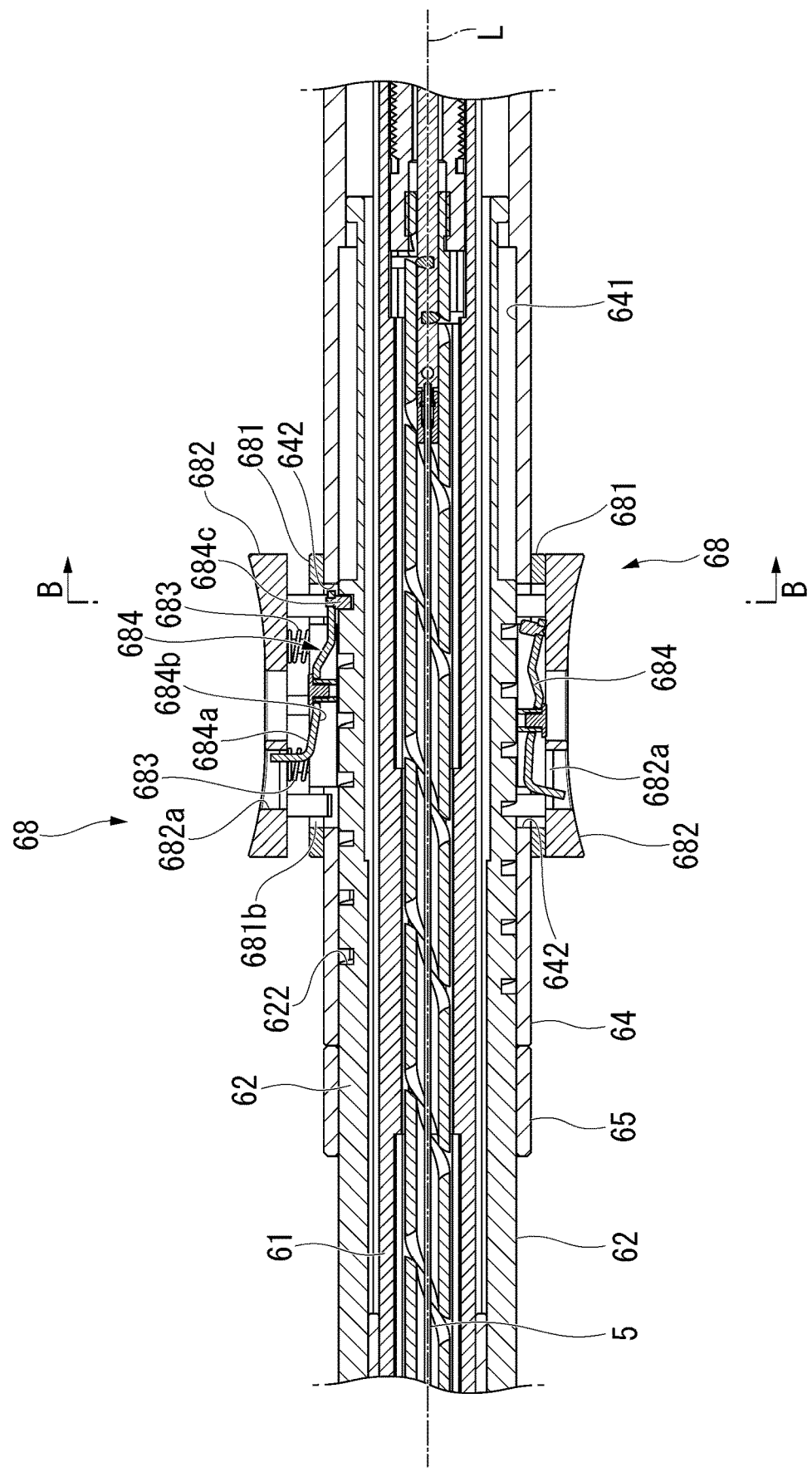
FIG. 13A is a partial cross-sectional view of the main manipulation part according to the embodiment.

As shown in FIG. 13A, a pair of side holes 642 are formed at positions of an outer circumference of the needle slider 64 opposite to each other in the radial direction. As shown in FIGS. 6 and 13A, a slide button unit 68 is provided in each of the pair of side holes 642. The slide button unit 68 is provided to switch between a state in which the needle slider 64 can advance and retract in the direction of the central axis L with respect to the main manipulation part main body 62 and a state in which the needle slider 64 can advance and retract while rotating about the central axis L. The slide button unit 68 in a state in which the needle slider 64 can advance and retract in the direction of the central axis L with respect to the main manipulation part main body 62 is shown at the lower side of FIG. 13A and the slide button unit 68 in a state in which the needle slider 64 can advance and retract while rotating about the central axis L with respect to the main manipulation part main body 62 is shown at the upper side of FIG. 13A. Actually, each of the pair of slide button units 68 is switched to one of a state shown at the upper side and a state shown at the lower side of FIG. 13A.

In the slide button unit 68, a base body 681 is fitted into the side hole 642 and fixed to the needle slider 64 and a button main body 682 is attached to an outer surface 681a of the base body 681 in a radial direction thereof. A spring member 683 is provided as a biasing member between the button main body 682 and the base body 681. The button main body 682 is biased in a direction in which the button main body 682 is away from the base body 681 outward in the radial direction by the spring member 683.

The slide button unit 68 further includes a plate 684 between the button main body 682 and the base body 681. The plate 684 is disposed to extend in the direction of the central axis L and a substantially intermediate part of the plate 684 in the direction of the central axis L is fixed to the base body 681. A hole 681b formed along the central axis L is formed in the base body 681. A distal end portion of the plate 684 is engaged with a slit 682a of the button main body 682 and a proximal end portion of the plate 684 is disposed in the hole 681b of the base body 681. A first surface 684a of the plate 684 faces the button main body 682 and a second surface 684b is located in the hole 681b and provided to face the main manipulation part main body 62. A locking pin (a locking part) 684c is provided at a proximal end portion of the plate 684 to protrude from the second surface 684b in a thickness direction of the plate 684 (inward in a radial direction of the base body 681). A helical groove (a second helical groove) 622 is formed in an outer circumstantial surface of an intermediate region of the main manipulation part main body 62 in the direction of the central axis L, and as shown in FIG. 13A, the locking pin 684c is switched between a state in which the locking pin 684c is engaged with the helical groove 622 and a state in which the locking pin 684c is not engaged with the helical groove 622.

Figure 13B:
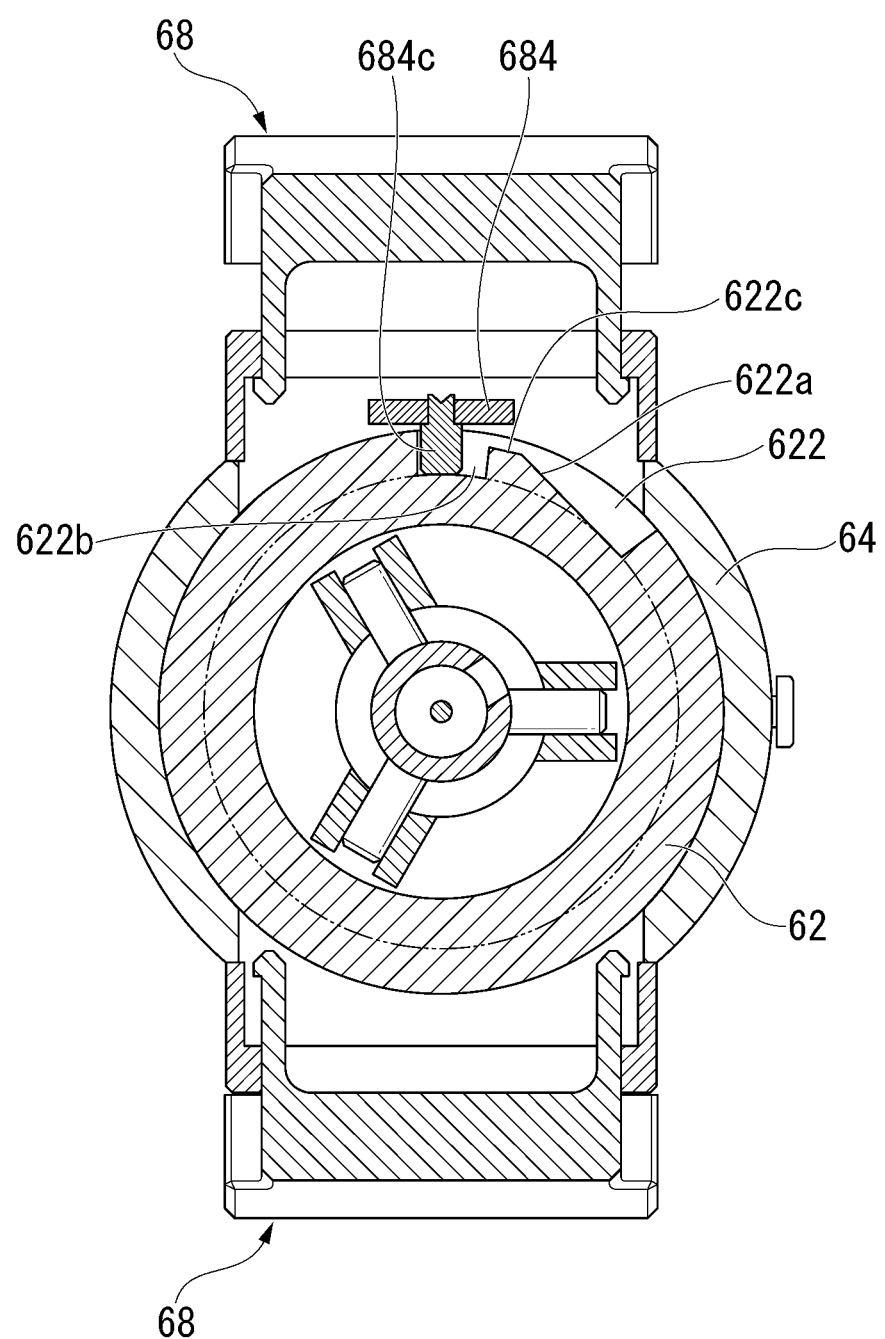
FIG. 13B is a cross-sectional view taken along line B-B in FIG. 13A.

FIG. 13B is a cross-sectional view of the main manipulation part main body 62 taken along line B-B of FIG. 13A. As shown in FIG. 13B, a step is formed at a proximal end portion of the helical groove 622 so that an oblique portion 622a and a dent portion 622b are adjacent to each other. To be specific, the dent portion 622b is formed at the proximal end of the helical groove 622 and the oblique portion 622a is formed closer to the distal end side of the helical groove 622 than the dent portion 622b so as to be continuous with the dent portion 622b. The oblique portion 622a is curvilinearly or linearly formed such that a groove depth of the helical groove 622 is gradually reduced toward the dent portion 622b and has a shallowest groove (a shallowest groove portion 622c) that is continuous with the dent portion 622b. On the other hand, the dent portion 622b is dented such that the groove depth sharply increases at a boundary between the dent portion 622b and the shallowest groove portion 622c. That is to say, an inner wall surface of the dent portion 622b at the boundary between the dent portion 622b and the shallowest groove portion 622c has an inclined angle larger than that of the oblique portion 622a in a helical direction following the helical groove 622. The dent portion 622b, the oblique portion 622a, and the locking pin 684c constitute a needle anti-movement mechanism. The needle anti-movement mechanism is configured to prevent movement of the locking pin 684c by the dent portion 622b and the oblique portion 622a. When an operator moves the needle slider 64 to the extreme proximal end side while rotating the needle slider 64, by the needle anti-movement mechanism, the locking pin 684c passes over the aforementioned oblique portion 622a and is fitted into the dent portion 622b and thus the locking pin 684c located at the dent portion 622b is put in a state in which the locking pin 684c cannot move.

When the operator presses the button main body 682 inward in the radial direction and pushes the button main body 682 until the button main body 682 comes into contact with the base body 681, the distal end portion of the plate 684 is pressed toward the main manipulation part main body 62 side. Accordingly, the proximal end portion of the plate 684 moves away from the main manipulation part main body 62 and the locking pin 684c is detached from the helical groove 622. In this state, since a connection relationship between the needle slider 64 and the main manipulation part main body 62 is released, a movement due to the needle slider 64 is not restricted by the helical groove 622 and the needle slider 64 is configured to be advanceable and retractable in the direction of the central axis L with respect to the main manipulation part main body 62.

In a state in which the button main body 682 is biased by the spring member 683 outward in the radial direction and is separated from the base body 681, the distal end portion of the plate 684 is pulled outward in the radial direction by the button main body 682 and the proximal end portion of the plate 684 is biased toward the main manipulation part main body 62 side. At this time, the locking pin 684c is fitted into the helical groove 622 formed in the outer circumstantial surface of the main manipulation part main body 62. In this state, the needle slider 64 is configured to be advanceable and retractable with respect to the main manipulation part main body 62 while rotating along the helical groove 622.

It should be noted that the locking pin 684c is capable of being moved to the proximal end of the helical groove 622 when the operator manipulates the needle slider 64 in a state in which the locking pin 684c is fitted into the helical groove 622. Therefore, the locking pin 684c passes over the oblique portion 622a and is fitted into the dent portion 622b in accordance with a manipulation of the needle slider 64 by the operator. In a state in which the locking pin 684c is fitted into the dent portion 622b, the locking pin 684c is biased toward the main manipulation part main body 62 side by the spring member 683. For this reason, as long as the locking pin 684c does not pass over the shallowest groove portion 622c of the oblique portion 622a, the needle slider 64 is not capable of being advanced while rotating along the helical groove 622. That is to say, the locking pin 684c is locked in a helical direction of the helical groove 622 and the movement of the needle slider 64 with respect to the main manipulation part main body 62 is prevented. In this state, as long as the operator presses the button main body 682 again inward in the radial direction and does not push the button main body 682 until the button main body 682 comes into contact with the base body 681, the fitting of the locking pin 684c into the dent portion 622b cannot be intentionally released and the needle slider 64 is put in a state in which the needle slider 64 is not capable of being advanced.

The first rotation knob 66 is a member that is rotationally manipulated by the operator when the tissue-fastening tool 2 is sent from the distal end of the needle tube 4. As shown in FIGS. 6, 7A, 7B, and 7C, the first rotation knob 66 is a cylindrical member and is attached to cover a side surface and a proximal end side of the needle slider end member 643. The first rotation knob 66 is rotatably attached to the needle slider end member 643. A female screw 661 is formed at a center of the first rotation knob 66 and is screwed to a male screw 572 which is cut in an outer circumference of the Luer joint 57. An engaging projection 643b that protrudes in the radial direction is formed in a through hole 643a at a substantially center of the needle slider end member 643. A linear groove 573 extending in the direction of the central axis L is formed in the outer circumference of the Luer joint 57. The engaging projection 643b is engaged with the linear groove 573. With this constitution, the Luer joint 57 and the first cam tube 61 fixed to the Luer joint 57 are advanced straight with respect to the first rotation knob 66 by the first rotation knob 66 being rotated. At the same time, the stylet 5 engaged with the first cam tube 61 is advanced straight with respect to the first rotation knob 66.

Figure 14:
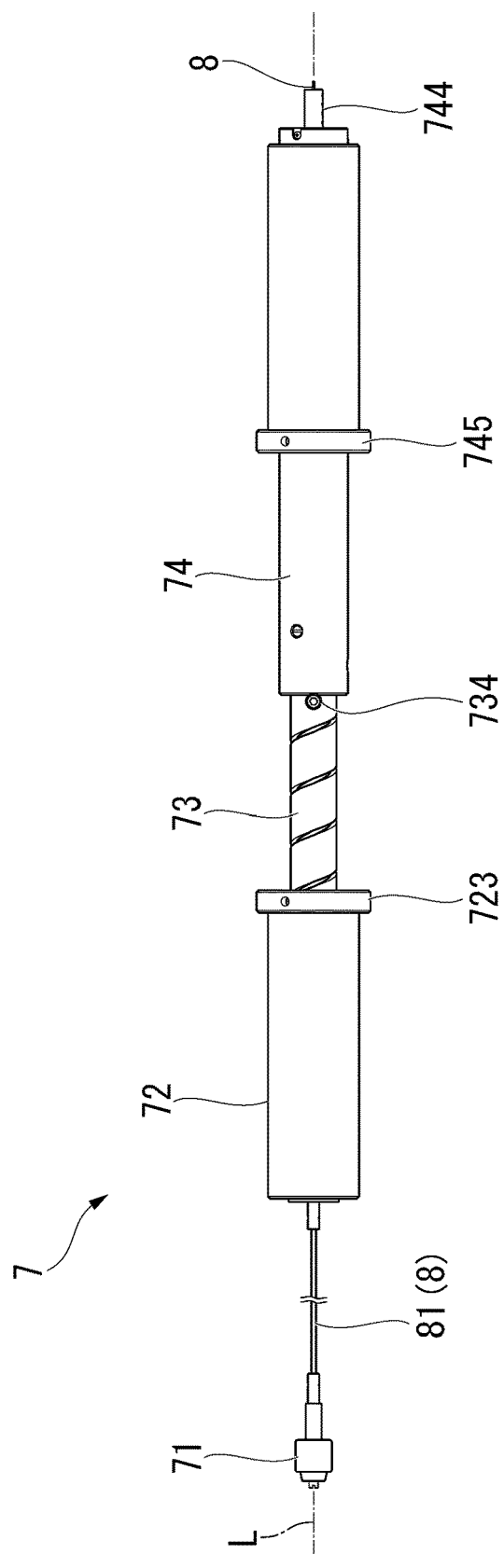
FIG. 14 is a side view of the auxiliary manipulation part according to the embodiment.

FIG. 14 is a side view of the auxiliary manipulation part 7 when viewed from a direction orthogonal to the central axis L. The auxiliary manipulation part 7 is disposed to be separated from the main manipulation part 6 and is connected to the main manipulation part 6 via the transmission member 8. The main manipulation part 6 and the auxiliary manipulation part 7 are configured to be separably connected to each other via the transmission member 8. The auxiliary manipulation part 7 advances and retracts the transmission member 8 to manipulate the movement of the stylet 5 in the main manipulation part 6. The auxiliary manipulation part 7 includes a manipulation coupling part 71, an auxiliary manipulation part main body 72, a second cam tube 73, and a rotation handle (a second manipulation input part) 74 in order from a distal end side thereof and the transmission member 8 is inserted throughout the entire length in the direction of the central axis L.

Figure 15A:
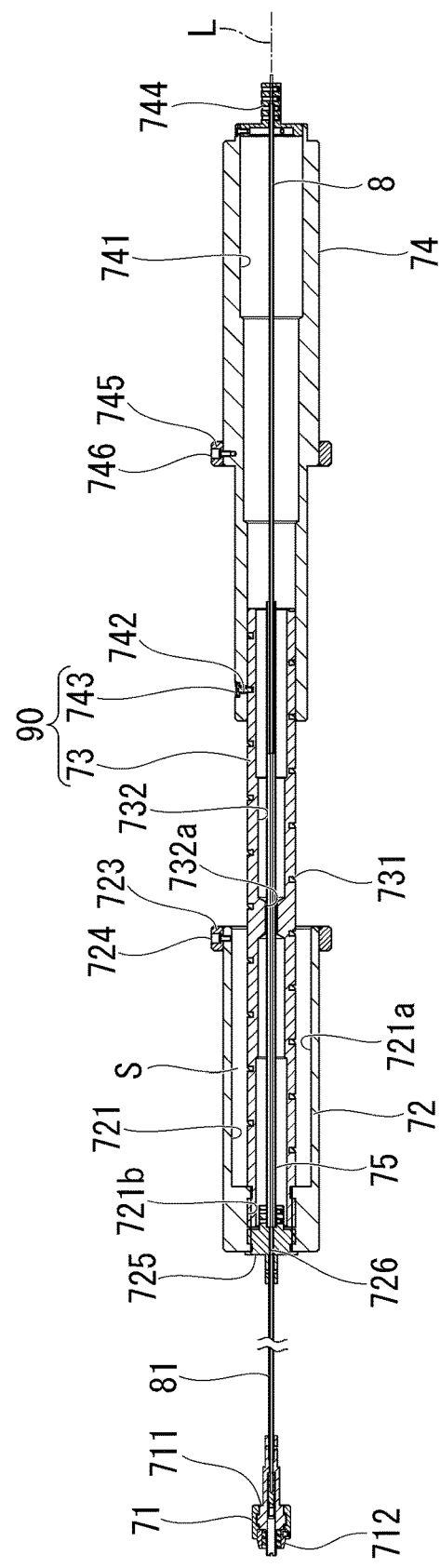
FIG. 15A is a cross-sectional view of the auxiliary manipulation part according to the embodiment.
Figure 15B:
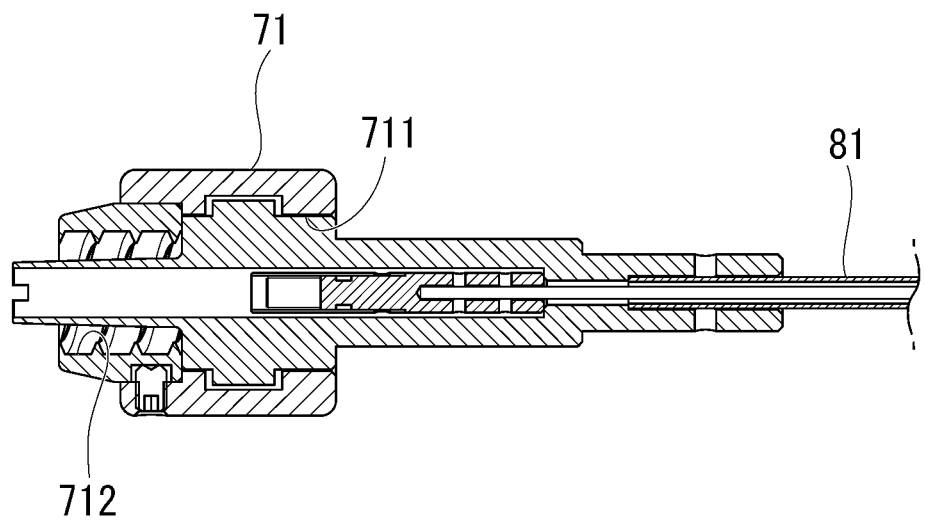
FIG. 15B is a cross-sectional view of a manipulation coupling part according to the embodiment.

FIG. 15A is a cross-sectional view of the auxiliary manipulation part 7 in a plane passing through the central axis L. FIG. 15B is a cross-sectional view of the manipulation coupling part 71. The manipulation coupling part 71 is a member that is the proximal end portion of the main manipulation part 6 and couples the proximal end portion of the stylet 5 to the distal end portion of the transmission member 8. A sixth insertion passage 711 extending in the direction of the central axis L is formed in the manipulation coupling part 71. A screw groove 712 capable of being screwed to a flange 574 of the Luer joint 57 (refer to FIG. 6) is formed around the central axis L on an inner circumferential surface of a distal end portion of the sixth insertion passage 711.

The transmission member 8 is a core material which is long and has flexibility (a flexible member). A distal end side from a substantially central part of the transmission member 8 in the direction of the central axis L is inserted into a cable tube 81 having flexibility. The transmission member 8 is a transmission member that transmits a manipulation input of the rotation handle 74 on the auxiliary manipulation part 7 to the main manipulation part 6.

As shown in FIG. 9, a stylet engagement part 82 is provided at the distal end of the transmission member 8. The stylet engagement part 82 includes two arms 82b extending in parallel with the direction of the central axis L from a base part 82a having a substantially cylindrical outer shape. The two arms 82b include planar parts 82c and 82d that face each other across the central axis L. A separation distance between the planar parts 82c and 82d in the radial direction (a direction orthogonal to the central axis L) is set to be slightly larger than a plate thickness of the proximal end engagement part 56 of the main manipulation part 6.

The transmission member 8 is inserted into the sixth insertion passage 711 to be advanceable, retractable, and rotatable with respect to the manipulation coupling part 71. In a state in which the auxiliary manipulation part 7 is not coupled to the main manipulation part 6, the distal end of the transmission member 8 is disposed at a substantially intermediate part of the sixth insertion passage 711 in the direction of the central axis L.

The stylet engagement part 82 is configured so that the stylet 5 and the transmission member 8 are engaged with each other when the proximal end engagement part 56 is inserted between the two arms 82b on the central axis L. When the stylet 5 and the transmission member 8 are engaged with each other, the planar parts 82c and 82d come into contact with the proximal end engagement part 56 and the rotational motion of the transmission member 8 can be transmitted to the stylet 5. Furthermore, the stylet 5 can advance when the transmission member 8 advances.

The auxiliary manipulation part main body 72 has a tubular shape and is disposed on a distal end side of the auxiliary manipulation part 7. As shown in FIG. 15A, a seventh insertion passage 721 extending in the direction of the central axis L is formed in the auxiliary manipulation part main body 72. The seventh insertion passage 721 includes a first region 721a on a proximal end side thereof and a second region 721b which is located closer to a distal end side thereof than the first region 721a and has an opening diameter smaller than an opening diameter of the first region 721a. A first ring member 723 is externally installed onto an outer circumstantial surface of a proximal end portion of the auxiliary manipulation part main body 72 and fixed to the outer circumstantial surface thereof by a screw 724.

A connector 725 is fixed to a distal end portion of the auxiliary manipulation part main body 72. To be specific, the connector 725 is inserted to block a distal end opening of the second region 721b of the seventh insertion passage 721 and fixed to the auxiliary manipulation part main body 72. An eighth insertion passage 726 is formed in the connector 725 along the central axis L and a distal end portion of a guide tube 75 to be described later is fixed to a proximal end side of the eighth insertion passage 726. The cable tube 81 is fixed to a distal end side of the eighth insertion passage 726. The transmission member 8 is inserted into the guide tube 75 and the cable tube 81 fixed in the eighth insertion passage 726 and extends to the manipulation coupling part 71.

Figure 16:
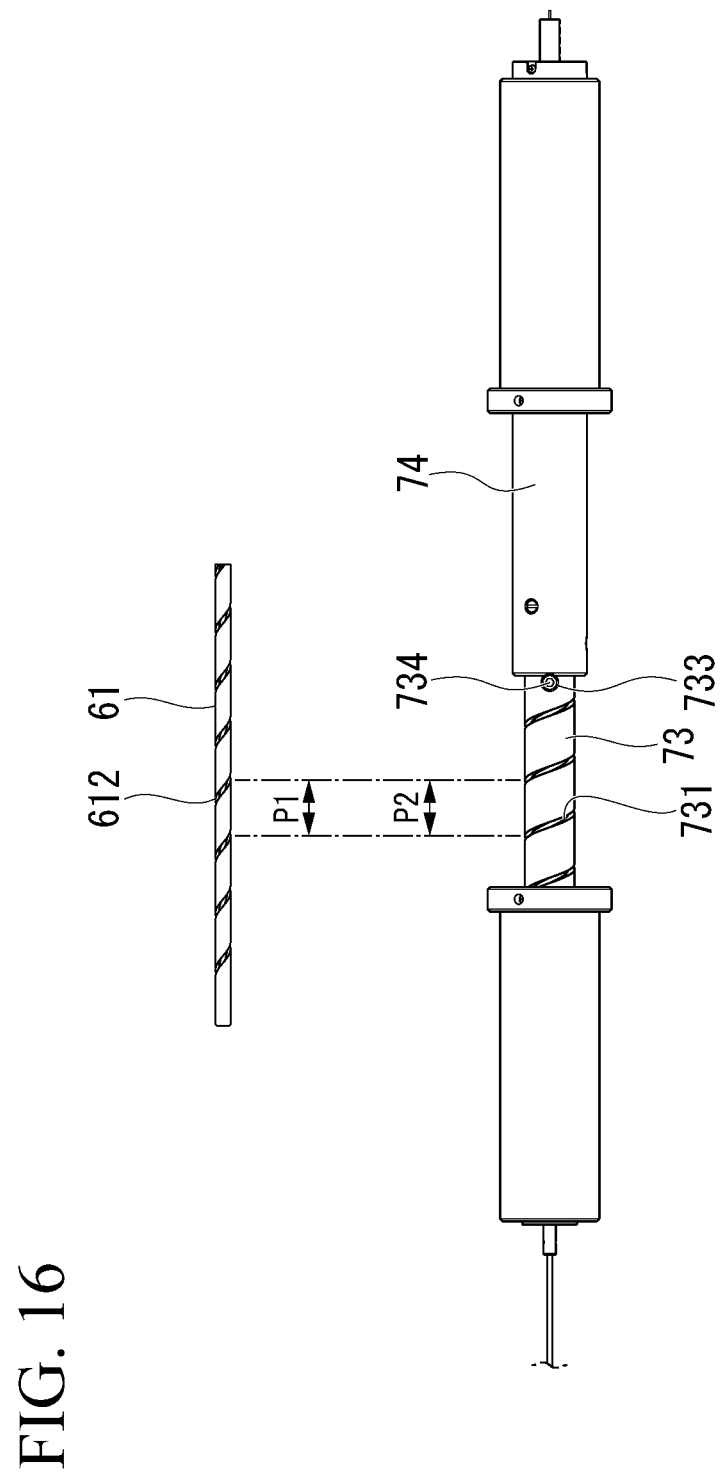
FIG. 16 is a diagram showing a relationship between the first guide passage and a second guide passage according to the embodiment.

The second cam tube 73 is a long tubular member and includes a second guide passage (a fourth helical groove) 731 constituted of a groove formed around the central axis L in a helical shape and distal and proximal end portions of the second guide passage 731 which are formed on an outer circumstantial surface thereof. As shown in FIG. 16, the second guide passage 731 of the second cam tube 73 and the first guide passage 612 of the first cam tube 61 are formed at the same helical pitches P1 and P2 and in the same rotational direction. A distal end side of the second cam tube 73 is inserted through the first region 721a of the seventh insertion passage 721 of the auxiliary manipulation part main body 72 and a distal end portion of the second cam tube 73 is fixed to the second region 721b. It should be noted that, shown in FIG. 16, the second cam tube 73 has a fitting hole 733 at a region in the outer circumstantial surface of the second cam tube 73 between grooves of the second guide passage 731. The fitting hole 733 is a hole formed through a wall surface of the second cam tube 73 such that a rod-like member 734 such as a split pin or a screw is fitted therein. The fitting hole 733 is formed to be exposed at a position closer to the distal end side of the second cam tube 73 than the distal end of the rotation handle 74 when the rotation handle 74 is moved to the extreme proximal end side, that is, when the second engaging pin 743 (to be described below) comes into contact with an end portion of the second guide passage 731 of the second cam tube 73. For this reason, as shown in FIG. 14, in the state in which the rotation handle 74 (to be described later) is moved to the extreme proximal end side, the rotation handle 74 cannot be moved forward due to the rod-like member 734 such as a split pin or a screw inserted into the fitting hole 733.

As shown in FIG. 15A, a gap S is formed between an inner circumferential surface of the first region 721a and an outer circumstantial surface of the second cam tube 73. The second cam tube 73 has a cam insertion passage 732 extending in the direction of the central axis L. A reduced diameter part 732a in which an opening diameter is reduced in a substantially central part in the direction of the central axis L is formed in the cam insertion passage 732.

The guide tube 75 having a length substantially equal to that of the second cam tube 73 is inserted into the cam insertion passage 732. A distal end portion of the guide tube 75 is fixed to the eighth insertion passage 726 of the connector 725 as described above. Since a proximal end side of the guide tube 75 is inserted through the reduced diameter part 732a of the cam insertion passage 732, the guide tube 75 is disposed so that a center thereof coincides with the central axis L. The transmission member 8 is inserted in the guide tube 75 to be advanceable and retractable. With this constitution, the transmission member 8 is supported on the central axis L to be advanceable and retractable in the auxiliary manipulation part 7.

As shown in FIGS. 14 and 15A, the rotation handle 74 is a tubular member and is disposed at a proximal end portion of the auxiliary manipulation part 7. In the rotation handle 74, a ninth insertion passage 741 extending in the direction of the central axis L is formed by an inner circumferential surface thereof. An opening diameter of a distal end side region of the ninth insertion passage 741 is set to be slightly larger than an outer diameter of the second cam tube 73. Three screw holes 742 communicating from an outer circumstantial surface of the rotation handle 74 into the ninth insertion passage 741 are formed at a distal end portion of the rotation handle 74 (two screw holes 742 are not shown in FIG. 15A). The screw holes 742 are provided at equal intervals in the circumferential direction at every ⅓ turn (an angle of 120 degrees) and is provided at equal intervals in the longitudinal direction at every ⅓ length of the aforementioned helical pitch.

The second cam tube 73 is inserted into the ninth insertion passage 741. In the state in which the second cam tube 73 is inserted into the ninth insertion passage 741 of the rotation handle 74, the second engaging pin (the second engaging part) 743 is screwed and fixed to each of the screw holes 742. Each of the screw holes 742 protrudes into the ninth insertion passage 741 when protruding inward in the radial direction from the inner circumferential surface of the rotation handle 74 and the second engaging pin 743 is slidably engaged in the second guide passage 731. An outer diameter of a distal end portion of the second engaging pin 743 is smaller than an opening width of the second guide passage 731. For this reason, the distal end portion of the second engaging pin 743 is configured to be relatively movable in the second guide passage 731 in accordance with the rotation of the rotation handle 74. The second cam tube 73 and the second engaging pin 743 constitute a second helical mechanism 90.

A fixing member 744 that covers a proximal end opening of the ninth insertion passage 741 is fixed to a proximal end portion of the rotation handle 74. The proximal end portion of the transmission member 8 and the proximal end portion of the rotation handle 74 are fixed to each other by the fixing member 744. Therefore, the proximal end portion of the transmission member 8 follows the manipulation of the rotation handle 74. That is to say, the second helical mechanism 90 advances the transmission member 8 while rotating the transmission member 8 with respect to the auxiliary manipulation part main body 72.

A second ring member 745 is externally installed onto an outer circumstantial surface of a substantially central part of the rotation handle 74 in the direction of the central axis L and fixed to the outer circumstantial surface thereof by a screw 746. An outer diameter of the rotation handle 74 on a position closer to a distal end side than the second ring member 745 is set to be slightly smaller than the opening diameter of the first region 721a of the seventh insertion passage 721.

In the indwelling device 1 having the aforementioned constitution, the main manipulation part 6 can perform various manipulations such as advancement, retraction, and rotation of the sheath 3, advancement and retraction of the needle tube 4, and advancement, retraction, and rotation of the stylet 5. The auxiliary manipulation part 7 is configured such that advancement, retraction, and rotational manipulation of the transmission member 8 can be performed and manipulation on the needle tube 4 cannot be performed.

Figure 17:
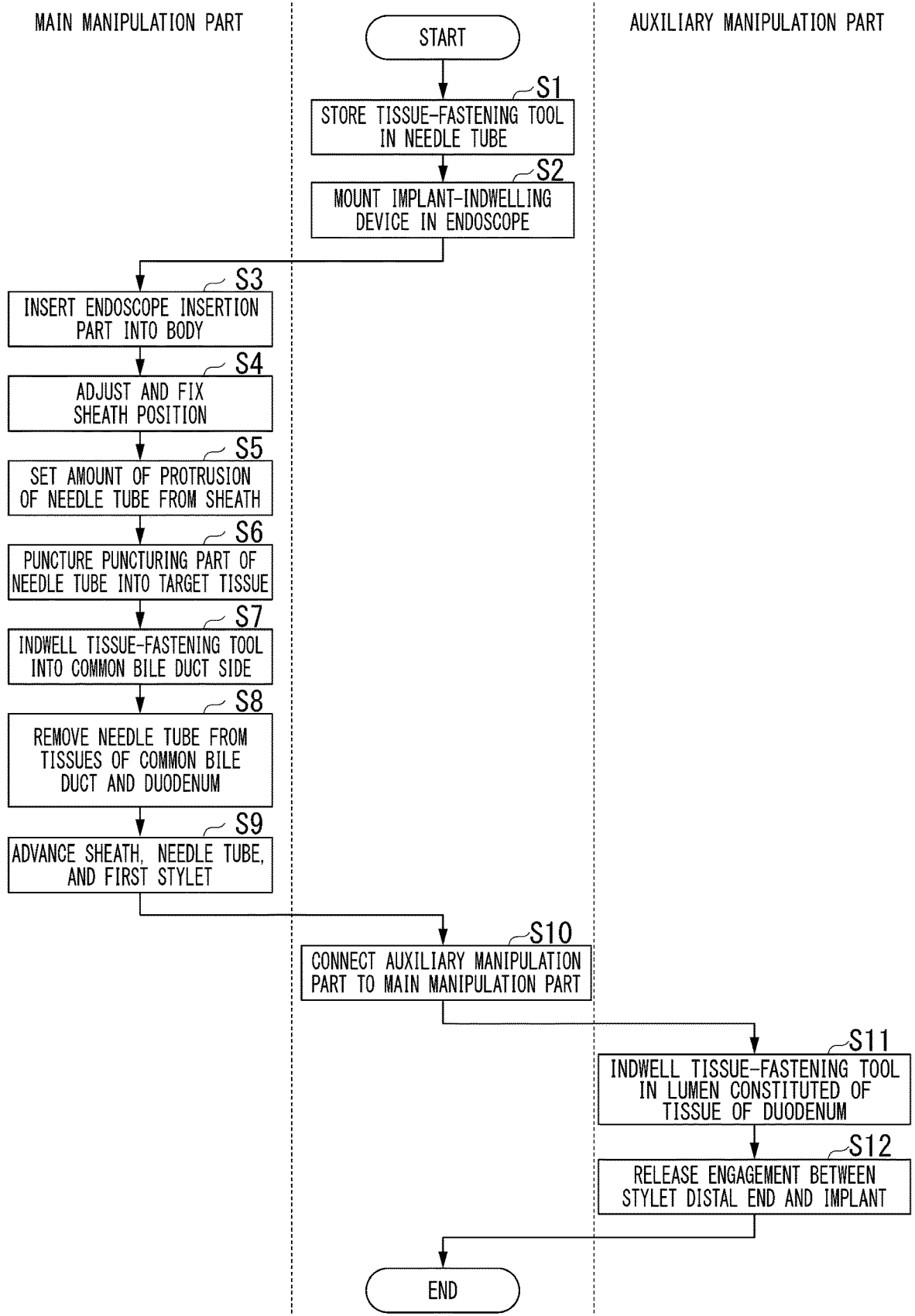
FIG. 17 is a flowchart of a procedure in which the tissue-fastening tool indwelling device according to the embodiment of is used.

With regard to the motion of the indwelling system according to this embodiment, a procedure of installing the indwelling device 1 in an ultrasonic endoscope (hereinafter referred to as an "endoscope"), passing the tissue-fastening tool 2 through the duodenal tissue D and the common bile duct tissue CBD, and indwelling the tissue-fastening tool 2 will be described below as an example. FIG. 17 is a flowchart showing the procedure of this embodiment.

The indwelling device 1 is configured such that a motion (a first motion) of the stylet 5 that moves from the proximal end side to the distal end side with respect to the needle tube 4 is capable of being manipulated by both of the main manipulation part 6 and the auxiliary manipulation part 7. Furthermore, the stylet 5 has a first state in which the stylet 5 is advanced straight with respect to the needle tube 4 and the sheath 3 until the entire distal end side region 201a of the coil region 201 of the implant 2 protrudes from the needle tube 4. Furthermore, the stylet 5 has a second state in which the stylet 5 is advanced straight while rotated until the entire proximal end side region 201b of the coil region 201 protrudes from the needle tube 4. It should be noted that a maximum movable amount of the stylet 5 (a maximum movable amount of the stylet 5 in the first state) in a direction along the longitudinal axis of the sheath 3 due to the main manipulation part 6 (the first rotation knob 66) may be set to be smaller than a maximum movable amount of the stylet 5 (a maximum movable amount of the stylet 5 in the second state) in a direction along the longitudinal axis of the sheath 3 due to the manipulation of the auxiliary manipulation part 7 (the rotation handle 74). On the other hand, the indwelling device 1 is configured such that manipulation (a second motion) of the needle tube 4 is performed only by the main manipulation part 6. This will be described in detail below.

Figure 18:
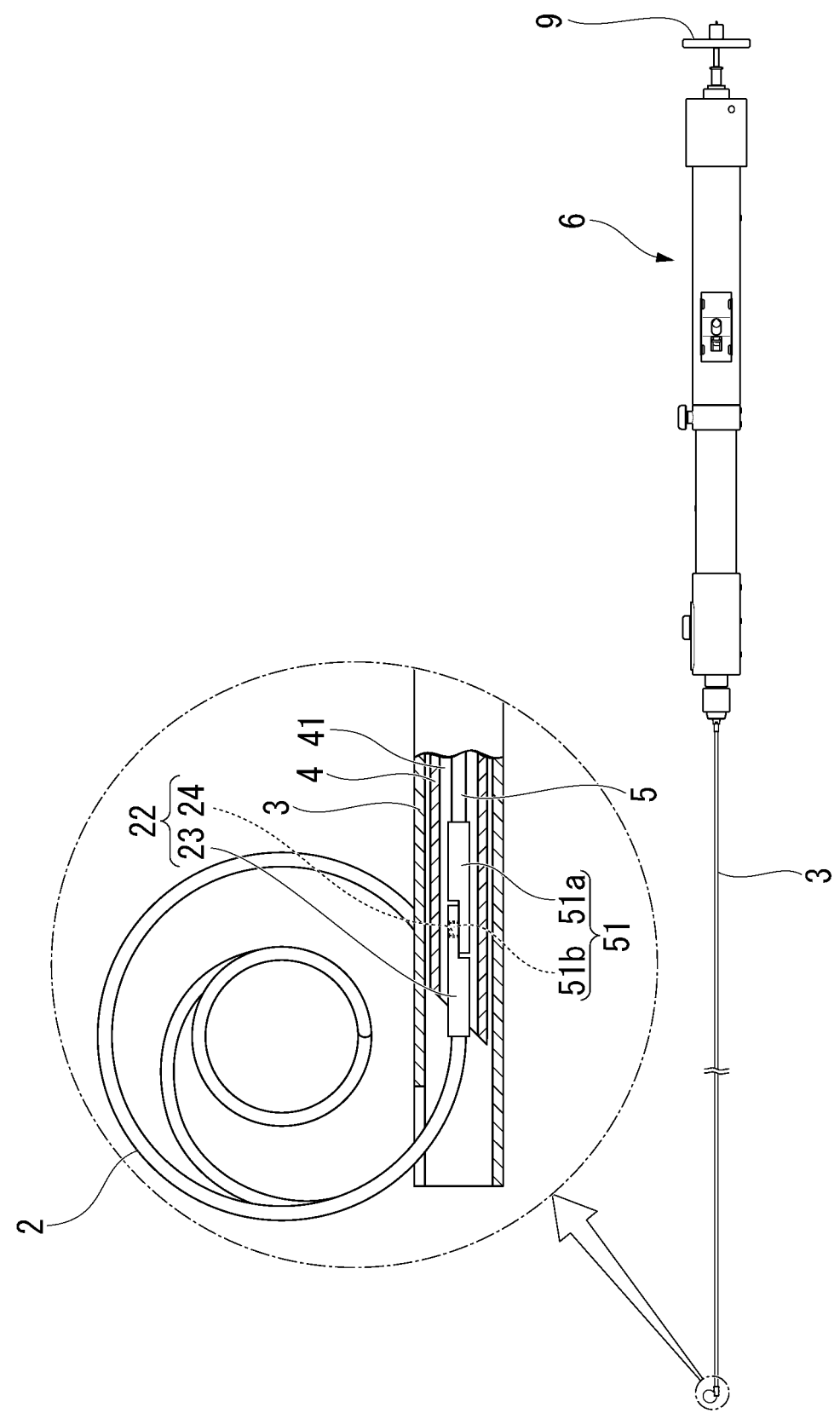
FIG. 18 is a side view showing an initial state of the main manipulation part according to the embodiment.

FIG. 18 is a side view showing an initial state of the main manipulation part 6. As shown in FIG. 18, in the tissue-fastening tool 2, the distal end portion of the stylet 5 and the proximal end portion of the tissue-fastening tool 2 are engaged with each other in the needle tube insertion passage 41 of the distal end portion of the needle tube 4 inserted into the sheath 3. The tissue-fastening tool 2 is provided to be projectable and retractable from the distal end of the needle tube 4. As shown in FIG. 18, a part of the tissue-fastening tool 2 located on a side closer to the distal end side than the coupling part with the stylet 5 protrudes from the distal end of the needle tube 4 and is disposed in a state in which the part thereof is restored to an indwelling shape.

The main manipulation part 6 is packed as a product in a state in which the jig 9 is inserted from the proximal end side thereof.

If the state in which the tissue-fastening tool 2 is loaded in the needle tube 4 throughout the entire length thereof is set as a packing state, a state in which the tissue-fastening tool 2 extends by the needle tube 4 continues for a long period of time. As a result, a restoring force applied to the tissue-fastening tool 2 in advance to a coiled curved shape thereof is likely to weaken. Furthermore, when the tissue-fastening tool 2 is independently packed separately from the main manipulation part 6, it is necessary for the user to perform a task of coupling the proximal end portion of the tissue-fastening tool 2 and the distal end portion of the stylet 5. However, since the tissue-fastening tool 2 is a very small member, the coupling task requires skill and time.

In consideration of the reduction of the shape restoring force of the tissue-fastening tool 2 and difficulty of a loading task, in this embodiment, as described above, the packing is performed in a state in which only the proximal end portion of the tissue-fastening tool 2 engaged with the stylet 5 is inserted into the needle tube 4 and other regions is located outside of the needle tube 4. This state is referred to as an initial state in this description. An example of a procedure for setting the initial state will be described below.

When the stylet 5 is moved to the extreme distal end side, the distal end engagement part 51 is exposed from the needle tube insertion passage 41. In this state, the initial state (packing state) is set by the protruding part 51b being engaged with the recessed part 24 of the tissue-fastening tool 2 and by the stylet 5 being moved to the proximal end side to store the distal end engagement part 51 in the needle tube 4. In the initial state, a connection state between the tissue-fastening tool 2 and the stylet 5 is maintained. At this time, a motion of pulling the stylet 5 using the jig 9 is performed.

Figure 19:
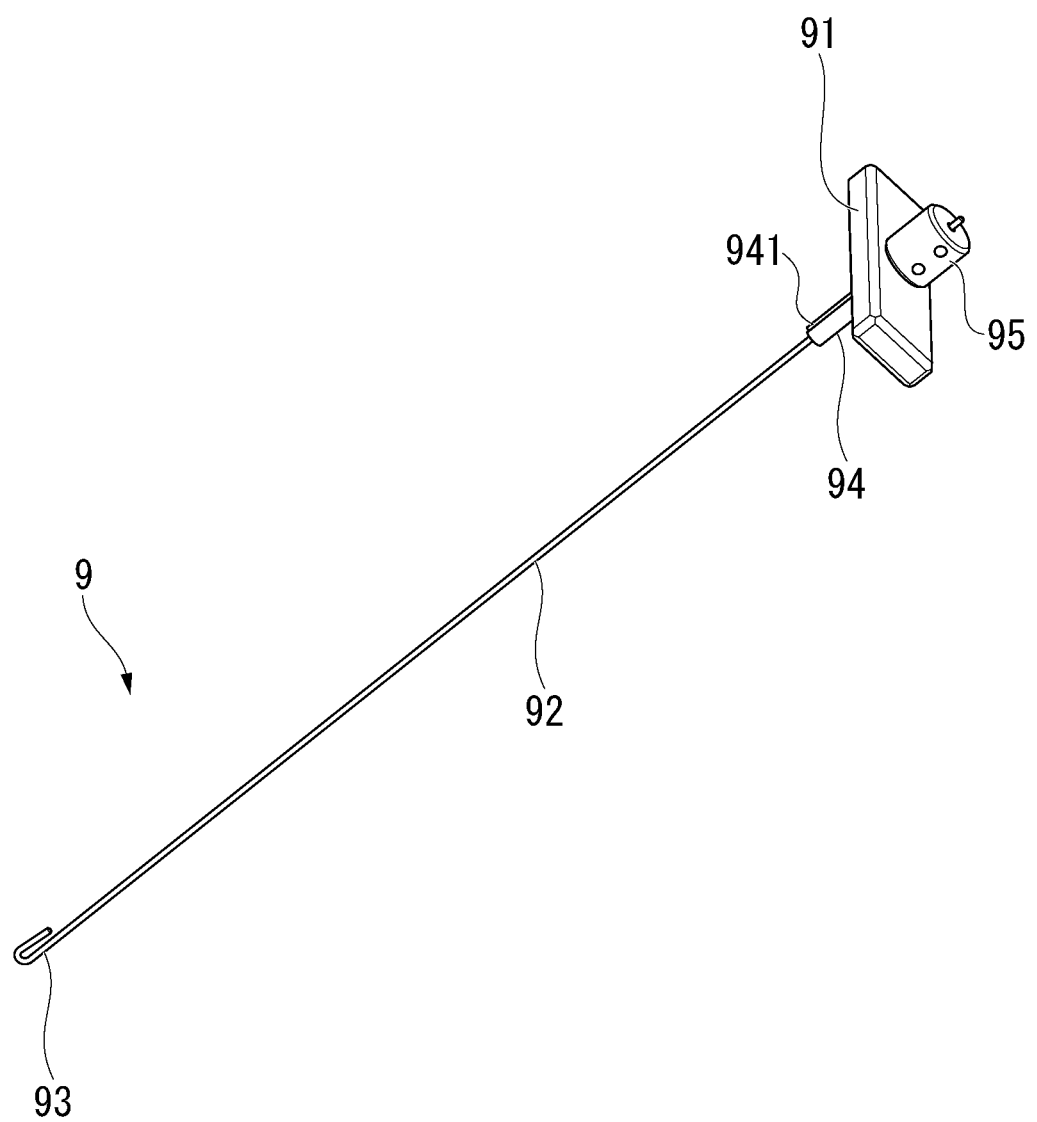
FIG. 19 is a perspective view of a jig according to the embodiment.

The jig 9 is installed in the main manipulation part 6 in the initial state (packing state). FIG. 19 is a perspective view showing the jig 9. As shown in FIG. 19, the jig 9 includes a jig handle 91, a rod-like insertion shaft (a shaft) 92, a jig side coupling part 93, and a shaft head 95. The insertion shaft 92 is fixed to a distal end side of the shaft head 95. At a center of the jig handle 91, a hole having a diameter slightly larger than that of the insertion shaft 92 and smaller than that of the shaft head 95 is opened and has the insertion shaft 92 inserted therein. The jig side coupling part 93 has a hook shape which is curved from a distal end of the insertion shaft 92 and extends toward a proximal end side thereof. The jig handle 91 is provided to be relatively rotatable with respect to the insertion shaft 92. A tubular jig stopper 94 is externally installed onto an outer circumference of a proximal end portion of the insertion shaft 92.

In the initial state, the jig side coupling part 93 is locked to the through hole of the proximal end engagement part 56 in the first cam tube 61. That is to say, the tissue-fastening tool 2 and the jig 9 are connected to each other via the stylet 5.

The proximal end engagement part 56 is disposed on the distal end side of the first cam tube 61. The insertion shaft 92 passes in the first cam tube 61 and extends toward the proximal end side and the jig handle 91 is exposed to the proximal end side of the main manipulation part 6. It should be noted that, at this time, the jig stopper 94 is not externally installed onto the insertion shaft 92. The insertion shaft 92 has a length that is greater than or equal to a length from the proximal end engagement part 56 to the proximal end of the Luer joint 57 when the stylet 5 is located at the extreme distal end side with respect to the needle tube 4. At this time, since the distal end of the stylet 5 is exposed to the outside of the needle tube 4 as described above, the distal end of the stylet 5 is engaged with the tissue-fastening tool 2. The proximal end portion of the tissue-fastening tool 2 is drawn into the needle tube 4 by pulling the jig 9 slightly toward the proximal end side to set the initial state. However, since there is a concern concerning the jig 9 moving toward the distal end side and the tissue-fastening tool 2 detached in this state, in order to prevent this, the jig 9 is prevented from moving to the distal end side by installing the jig stopper 94. Since a notch 941 is formed in the jig stopper 94 in the direction of the central axis L, the jig stopper 94 can be externally installed onto the insertion shaft 92 from a side thereof. Thus, the initial state (the packing state) is completed. After being sterilized by a manufacturer, a product is shipped.

First, the user performs a preparatory process (Step S1) of pulling and entirely putting the tissue-fastening tool 2 into the needle tube 4. Here, the user refers to an operator and an assistant who assists a treatment of the operator. The preparatory process may be performed by the operator or by the assistant. In the following description, a rotational direction when the user performs a rotational manipulation of each part of the main manipulation part 6 and the auxiliary manipulation part 7 is represented by a rotational direction viewed from the proximal end to the distal end in the direction of the central axis L.

First, the user rotates the first rotation knob 66 of the main manipulation part 6 in a right direction. When the first rotation knob 66 rotates in the right direction, the Luer joint 57 and the first cam tube 61 fixed to the Luer joint 57 move to the proximal end side. Since the first engaging pins 55 of the stylet 5 is engaged with both the first guide passage 612 and the guide slit 673 of the needle guide 67, when the first cam tube 61 moves toward the proximal end side, the stylet 5 also moves toward the proximal end side. As a result, the tissue-fastening tool 2 is pulled toward the proximal end side in the needle tube 4. When the user continues to rotate first rotation knob 66 right, the female screw 661 comes into contact with a distal end side terminal of the male screw 572 of the Luer joint 57 screwed into the female screw 661, the first rotation knob 66 cannot rotate any more, and the movement of the Luer joint 57 to the proximal end side cannot be performed. Thus, the user perceives that the substantially intermediate part of the tissue-fastening tool 2 in the longitudinal direction has been drawn into the needle tube 4.

Subsequently, the tissue-fastening tool 2 is drawn into the needle tube 4 using the jig 9. When the user pulls the jig handle 91 of the jig 9 toward the proximal side in the direction of the central axis L, a pulling force in a proximal end direction acts on the stylet 5. At this time, since the first engaging pins 55 slides along the first guide passage 612, the stylet 5 moves toward the proximal end side while rotating and the tissue-fastening tool 2 is further drawn into the needle tube 4. The jig handle 91 is provided to be relatively rotatable with respect to the insertion shaft 92. For this reason, at a time of a manipulation in which the user pulls the jig handle 91 in the direction of the central axis L, the insertion shaft 92 relatively rotates with respect to the jig handle 91 to follow the rotation of the stylet 5. At this time, since the first engaging pins 55 is also engaged with the guide slit 673 of the needle guide 67, the needle guide 67 is simultaneously rotated. Since the tissue-fastening tool 2 generates a strong force to return to an original coil shape thereof by being drawn into the needle tube 4, the needle tube 4 receives the strong force from the tissue-fastening tool 2. Therefore, the movement of the needle tube 4 in the rotational direction may be made to follow the movement of the tissue-fastening tool 2 in order to easily draw the tissue-fastening tool 2 into the needle tube 4. For this reason, the needle tube 4 is attached to the needle guide 67 to be relatively rotatable and not to be advanceable and retractable. The tissue-fastening tool 2 can be loaded into the needle tube 4 while rotating due to the motion of pulling the jig handle 91 toward the proximal end side in a linear direction along the central axis L.

When the user continues to further draw the jig 9 toward the proximal side, the tissue-fastening tool 2 is gradually stored in the needle tube 4 and one of the first engaging pins 55 that is disposed closest to the proximal end side comes into contact with an end face on the distal end side of the Luer joint 57 immediately after the distal end of the tissue-fastening tool 2 is stored in the needle tube 4. For this reason, the stylet 5 can no longer move toward the proximal end side and the jig 9 can no longer be drawn toward the proximal side. Thus, the user perceives that the loading of the tissue-fastening tool 2 has been completed. At the same time, since the proximal end engagement part 56 is exposed to the outside, the operator releases the engagement between the jig 9 and the proximal end engagement part 56 to detach the jig 9. Thus, the preparatory process is completed.

In this way, in the indwelling device 1 according to this embodiment, since the tissue-fastening tool 2 is loaded using the jig 9, it is not required to provide a mechanism for drawing the tissue-fastening tool 2 into the needle tube 4 in the main manipulation part 6 and it is possible to reduce a size of the main manipulation part.

Figure 20:
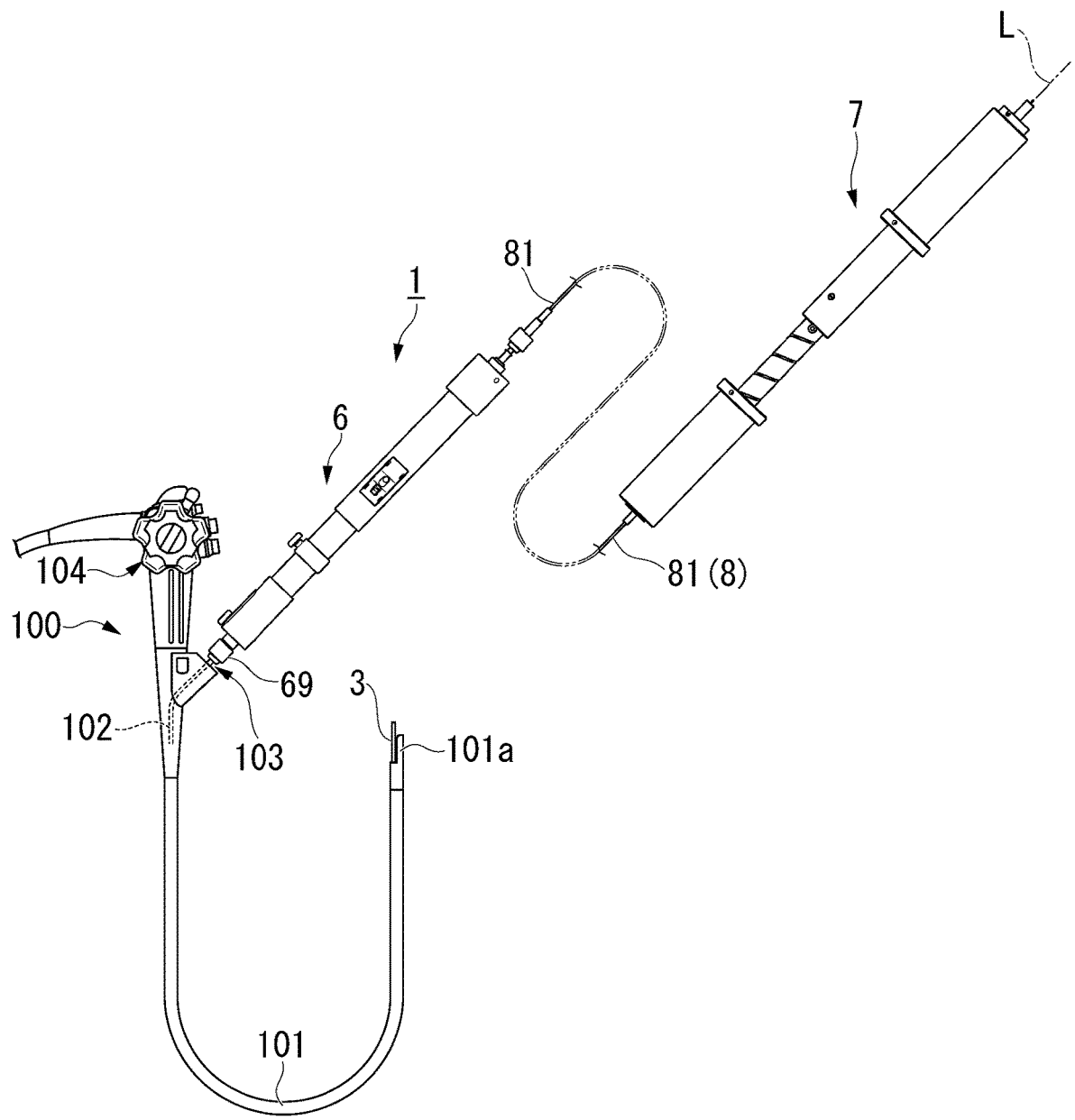
FIG. 20 is a diagram showing a state in which the tissue-fastening tool indwelling device according to the embodiment is installed in an endoscope.

Subsequently, the main manipulation part 6 is installed in the endoscope 100 and fixed thereto (Step S2). The sheath 3 and the needle tube 4 are inserted into the treatment tool channel 102 of the endoscope insertion part 101, and as shown in FIG. 20, the main manipulation part 6 is fixed to the manipulation part 104 of the endoscope 100 by screw-engaging the mounting part 69 provided at the distal end of the sheath slider 63 of the main manipulation part 6 with the port 103 of the treatment tool channel 102 of the endoscope 100. In Step S2, the operator and the assistant cooperate to perform the manipulation.

Figure 21:
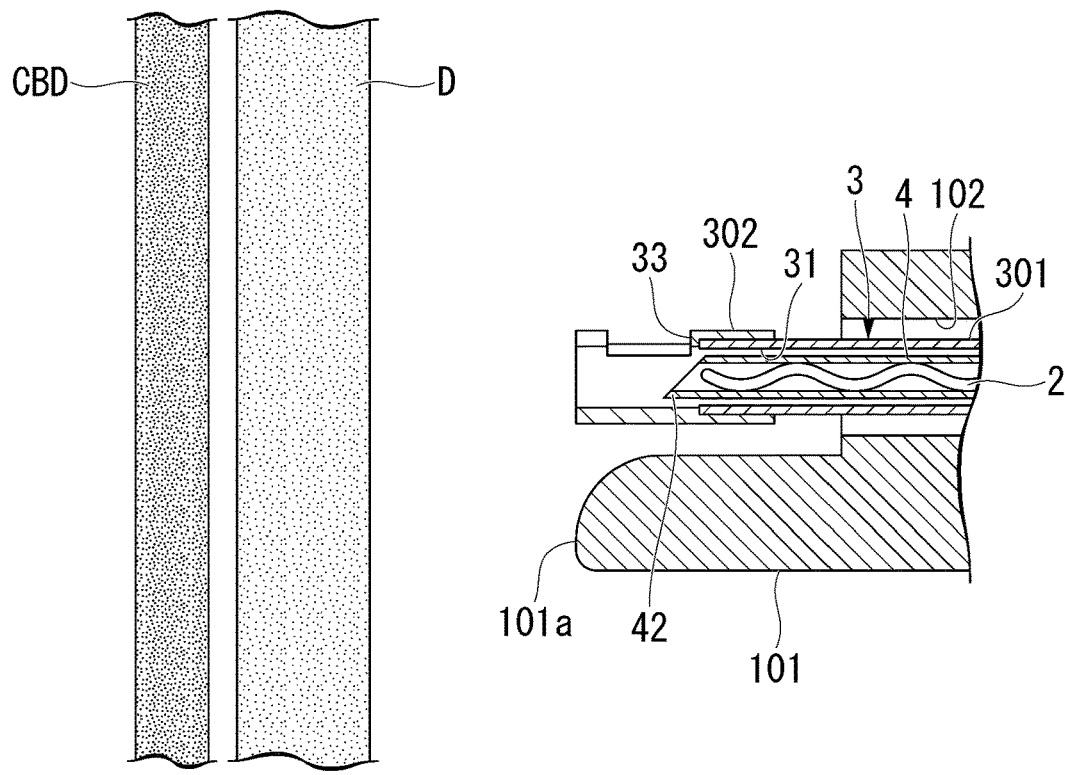
FIG. 21 is a side view showing a usage mode of the tissue-fastening tool indwelling device according to the embodiment.

Manipulations from Step S3 to Step S9 are performed by the operator. FIGS. 21 to 27 are diagrams showing aspects on the distal end side of the endoscope insertion part 101 when using the indwelling device 1. As shown in FIG. 21, the operator inserts the endoscope insertion part 101 into a treatment target site in a body (Step S3). A distal end of the endoscope insertion part 101 is inserted into the vicinity of the duodenal tissue D which is a target tissue. Steps S2 and Step S3 may be performed in reverse order.

Subsequently, a position of the distal end of the sheath 3 with respect to the distal end of the endoscope insertion part 101 is adjusted (Step S4). The operator loosens the fixing knob 634, advances and retracts the main manipulation part main body 62 in the direction of the central axis L with respect to the sheath slider 63, and performs adjustment so that the position of the distal end of the sheath 3 in the direction of the central axis L is at a predetermined position with respect to the distal end of the endoscope insertion part 101. FIG. 21 shows a state in which the distal end position of the sheath 3 in the direction of the central axis L coincides with the distal end of the endoscope insertion part 101. When the distal end position of the sheath 3 is determined, the operator tightens the fixing knob 634 to fix the position of the sheath 3.

Figure 22:
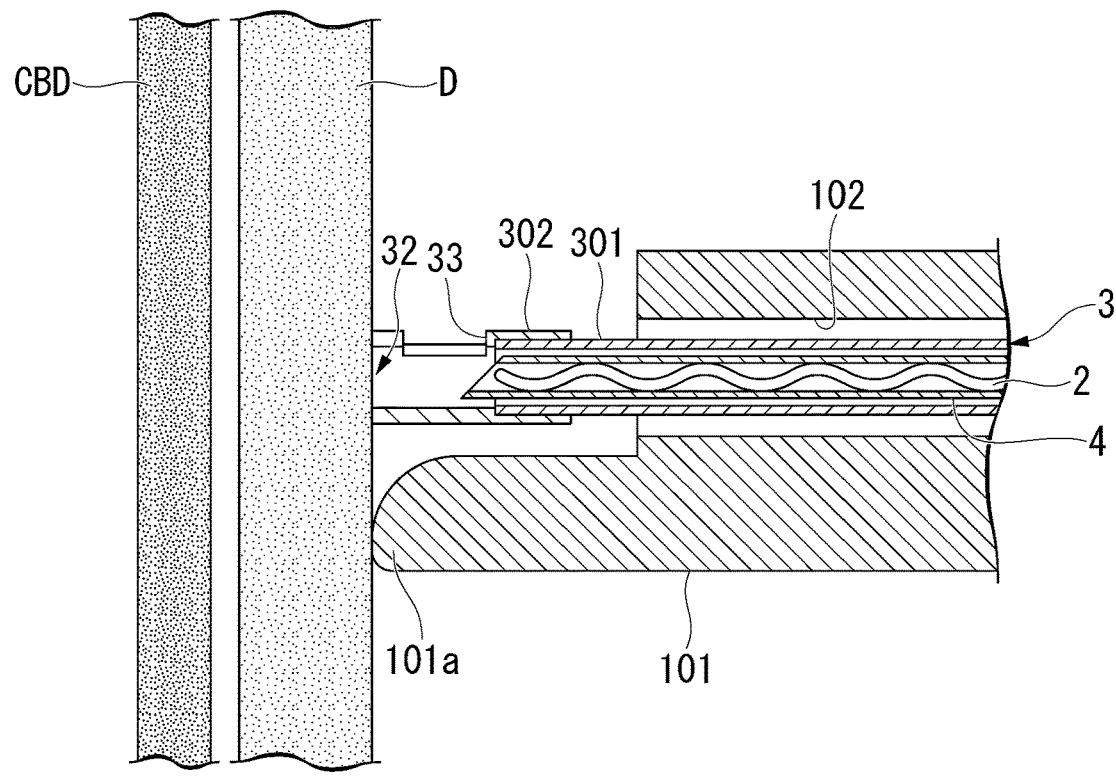
FIG. 22 is a side view showing the usage mode of the tissue-fastening tool indwelling device according to the embodiment.

As shown in FIG. 22, the operator brings the endoscope insertion part 101 and the distal end opening portion 32 of the sheath 3 into contact with the duodenal tissue D. An ultrasonic transducer 101a is provided at the distal end of the endoscope insertion part 101. For this reason, in a subsequent treatment, a state in which the distal end of the endoscope insertion part 101 is in contact with the duodenal tissue D is maintained and the operator performs the treatment while checking an ultrasonic image.

Subsequently, an amount of protrusion of the needle tube 4 from the distal end opening portion 32 of the sheath 3 in the direction of the central axis L is set (Step S5). When the operator loosens the needle stopper screw 652, the needle slider stopper 65 can slide. After sliding the needle slider stopper 65 toward the distal end side depending on a length (an amount of protrusion of the needle tube 4 from the sheath 3) by which the puncturing part 42 of the needle tube 4 is desired to puncture into the tissue, the operator tightens the needle stopper screw 652 to fix the needle slider stopper 65. By the manipulation, a puncture length of the puncturing part 42 of the needle tube 4 is set. At this time, the movement of the needle slider 64 is restricted by the slide button unit 68 and the needle slider 64 does not move linearly.

Figure 23:
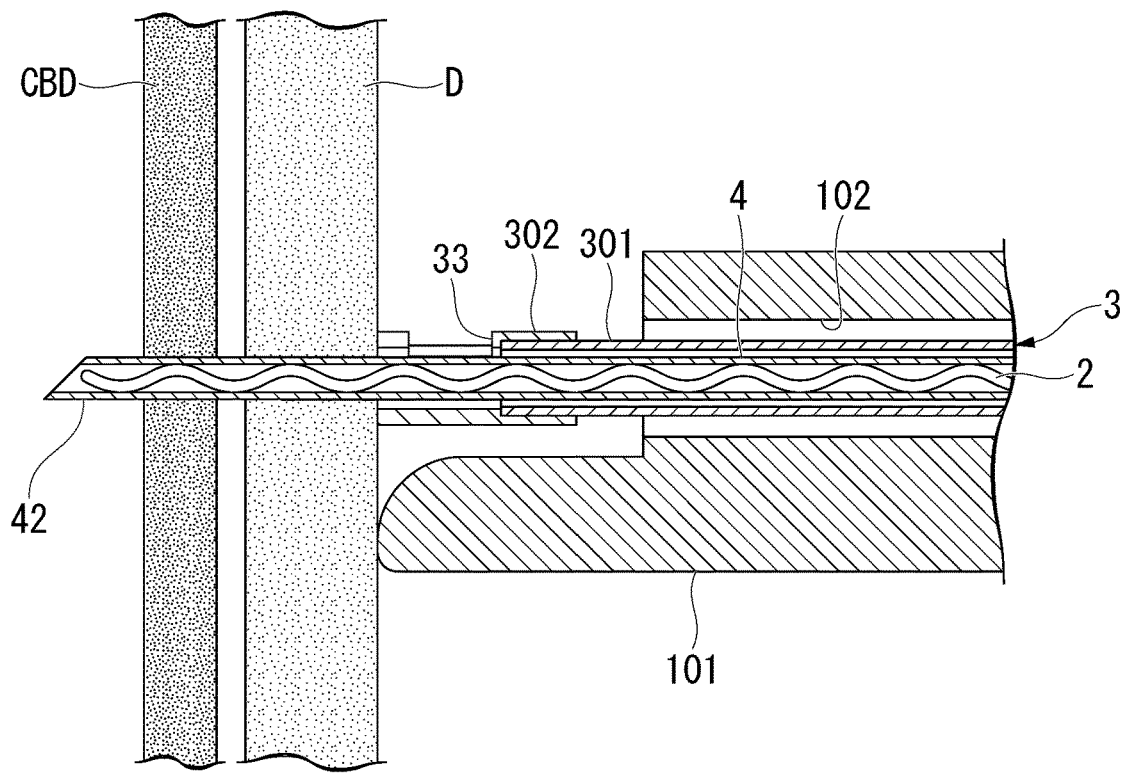
FIG. 23 is a side view showing the usage mode of the tissue-fastening tool indwelling device according to the embodiment.

Subsequently, as shown in FIG. 23, the puncturing part 42 of the needle tube 4 punctures the target tissue (Step S6). When the operator pushes the button main body 682 of the slide button unit 68 toward the central axis L side, a restriction of an advancement and retraction movement of the needle slider 64 is released and the needle slider 64 enters a state of being advanceable and retractable in the direction of the central axis L with respect to the main manipulation part main body 62. Thereafter, the operator advances the needle slider 64 in a linear direction until the needle slider 64 comes into contact with the needle slider stopper 65. Since the needle slider 64 and the needle tube 4 are connected to each other via the needle guide 67 such that relative positions thereof in the direction of the central axis L are invariable, the needle tube 4 advances straight with the advancement of the needle slider 64. Thus, the puncturing part 42 of the needle tube 4 protrudes from the distal end of the sheath 3 and punctures the duodenal tissue D and the common bile duct tissue CBD, which are target tissues. It should be noted that, when the operator releases (releases the pressure to the button main body 682) his or her finger from the slide button unit 68, the slide button unit 68 moves in a direction in which the button main body 682 is separated from the outer side of the needle slider 64 in the radial direction by a biasing force of the spring member 683 and the locking pin 684c is pressed against an outer surface of the main manipulation part main body 62.

Figure 24:
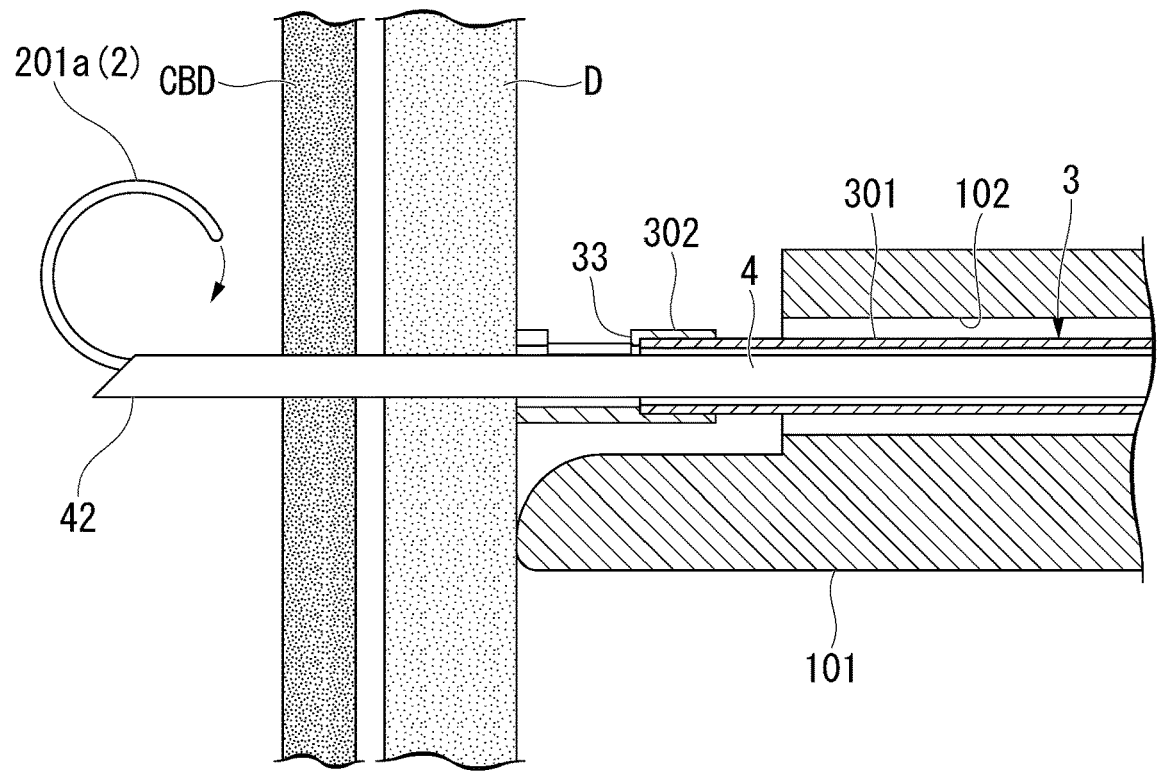
FIG. 24 is a side view showing the usage mode of the tissue-fastening tool indwelling device according to the embodiment.

Subsequently, the tissue-fastening tool 2 is indwelled into a common bile duct side (Step S7). As shown in FIG. 24, the tissue-fastening tool 2 is caused to protrude from the needle tube 4. The operator rotates the first rotation knob 66 left. In a step in which a left rotational manipulation of the first rotation knob 66 is started, the needle slider 64 is also rotated left with the first rotation knob 66 until the locking pin 684c of the plate 684 is engaged with the helical groove 622 of the main manipulation part main body 62. Shortly, when the locking pin 684c is engaged with the helical groove 622, although the needle slider 64 about to advance toward the distal end side while rotating along the helical groove 622, the needle slider 64 neither rotates nor advances because the needle slider 64 is in contact with the needle slider stopper 65. For this reason, after the locking pin 684c is engaged with the helical groove 622, only the first rotation knob 66 is rotated. When the first rotation knob 66 is rotated with respect to the needle slider 64, the Luer joint 57 and the first cam tube 61 are linearly sent to the distal end side. At this time, the end face of the Luer joint 57 on the distal end side thereof and one of the first engaging pins 55 on the extreme proximal end side come into contact with each other. Thus, the stylet 5 is linearly sent to the distal end side while causing the first engaging pins 55 to slide along a slit surface of the guide slit 673 by pushing out the first engaging pins 55 by a distal end face of the Luer joint 57. As described above, a distal end side region 201a of a coil of the tissue-fastening tool 2 is linearly sent from the distal end of the needle tube 4 into the common bile duct. That is to say, in the first state, the stylet 5 linearly advances the distal end side region 201a of the tissue-fastening tool 2 in the needle tube 4 without rotating the distal end side region 201a so that the distal end side region 201a is capable of being sent from the distal end 42 of the needle tube 4 into the common bile duct.

When a proximal end side end face of the linear groove 573 of the Luer joint 57 comes into contact with a proximal end side end face of the engaging projection 643b of the needle slider end member 643 in time, the Luer joint 57 does no longer move toward the distal end side and the first rotation knob 66 does not rotate. That is to say, the proximal end side end face of the linear groove 573 of the Luer joint 57 functions as a restriction portion for restricting the rotation due to the first rotation knob 66. A length in the direction of the central axis L between the proximal end side end face of the linear groove 573 of the Luer joint 57 and the proximal end side end face of the engaging projection 643b of the needle slider end member 643 is set depending on a length of the metal element wire constituting the distal end side region 201a of the tissue-fastening tool 2. For this reason, when the distal end 27 of the tissue-fastening tool 2 protrudes from a needle tip of the needle tube 4 and there is a positional relationship in which the proximal end 21 of the tissue-fastening tool 2 is located in the needle tube 4, the proximal end side end face of the linear groove 573 of the Luer joint 57 pushes onto the proximal end side end face of the engaging projection 643b of the needle slider end member 643 and the rotation due to the first rotation knob 66 is restricted. It should be noted that, as the first rotation knob 66 does not rotate, the operator can perceive that the process of indwelling the metal element wire of the tissue-fastening tool 2 on the common bile duct side by an amount of the distal end side region 201a is completed.

Figure 25:
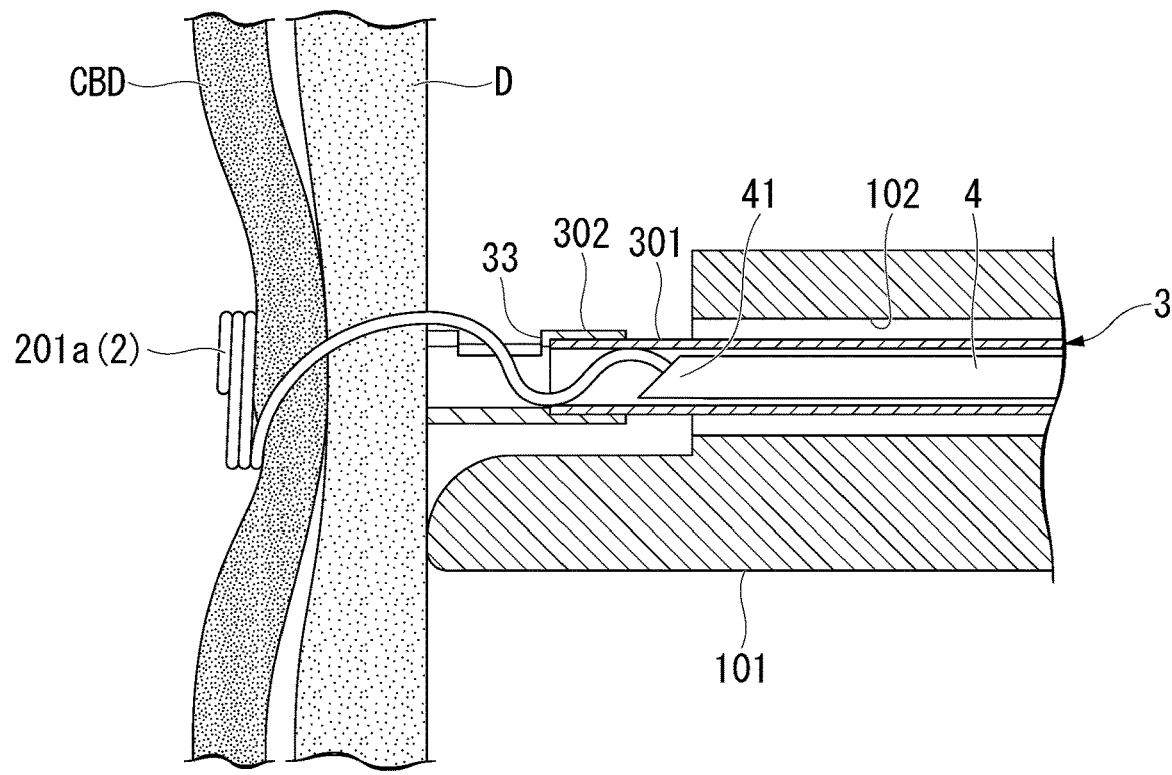
FIG. 25 is a side view showing the usage mode of the tissue-fastening tool indwelling device according to the embodiment.

Subsequently, as shown in FIG. 25, the needle tube 4 is removed from the common bile duct tissue CBD and the duodenal tissue D (Step S8). When the needle tube 4 is removed, as the distal end of the needle tube 4 is pulled out of the common bile duct tissue CBD, the distal end side region 201a of the tissue-fastening tool 2 is inclined and a circumferential direction of the coil comes into close contact with the common bile duct tissue CBD. At this time, since there is a case in which the distal end side region 201a is inclined in a direction different from a predetermined direction of the coil. When the distal end side region 201a is inclined in the different direction, the tissue-fastening tool 2 is not in an ideal indwelling mode, but a state of the coil on the common bile duct side cannot be visually recognized. Thus, a manipulation of correcting a direction of the distal end side region 201a to the predetermined direction is necessarily performed.

The operator rotates the needle slider 64 right. Since the locking pin 684c of the plate 684 is engaged with the helical groove 622 of the main manipulation part main body 62, when the needle slider 64 is rotated right, the needle slider 64 moves toward the proximal end side while rotating along the helical groove 622. The Luer joint 57 and the first cam tube 61 also moves toward the proximal end side together with the needle slider 64 while rotating right. Since the first guide passage 612 of the first cam tube 61 is formed in a right screw direction, an inner surface of the first guide passage 612 imparts a vector force in a direction of the proximal end side to the first engaging pins 55 of the stylet 5 due to a right rotation of the first cam tube 61. When the operator moves the needle slider 64 to the extreme proximal end side while rotating the needle slider 64, the locking pin 684c passes over the aforementioned oblique portion 622a and fitted into the dent portion 622b. For this reason, as long as the operator does not press the button main body 682 inward in the radial direction to be pushed in until the button main body 682 comes into contact with the base body 681, the fitting of the locking pin 684c into the dent portion 622b is not capable of being intentionally released and the needle slider 64 is not capable of being advanced.

Also, since one of the first engaging pins 55 on the extreme proximal end side is in contact with the end face of the Luer joint 57 on the distal end side thereof, the stylet 5 basically moves toward the proximal end side while rotating right together with the needle slider 64. At this time, the needle guide 67 also moves toward the proximal end side while rotating right together with the needle slider 64. Since the needle tube 4 is rotatably supported by the needle guide 67, the needle tube 4 moves toward the proximal end side together with the needle slider 64, but the movement of the needle tube 4 in the rotational direction is not related to the needle slider 64. In an actual procedure, since the endoscope insertion part 101 has a complex curved shape, the needle tube 4 inserted into the treatment tool channel 102 is also curved in a complex shape. As described above, a material of the needle tube 4 is a metal and it is difficult to perform a manipulation which rotates the needle tube 4 in a state of being curved in the complex shape because a very strong force is necessary. For this reason, even if the needle slider 64 moves toward the proximal end side while rotating, the needle tube 4 is configured to only follow the movement toward the proximal end side without rotating.

As shown in FIG. 7A, the sheath 3 is fixed to the sheath guide 623 via the sheath fixing part 625. The sheath guide 623 is rotatably supported by the main manipulation part main body 62. As shown in FIG. 7D, the first slits 623b of the sheath guide 623 is fitted onto the ribs 673a formed on a radial outside of the circumference of the guide slit 673 of the needle guide 67 to follow only the rotational direction. With such a constitution, when the needle slider 64 is moved toward the proximal end side while being rotated right, the sheath 3 only follows the rotation.

With the aforementioned motion, the sheath 3 and the stylet 5 rotate while the needle tube 4 is pulled back. When the puncturing part 42 of the needle tube 4 is stored in the lumen 31 of the sheath 3, a wire of the tissue-fastening tool 2 enters the slit 33 of the sheath 3. When the sheath 3 rotates in a predetermined direction in a state in which the wire of the tissue-fastening tool 2 is locked to the slit 33, the distal end side region 201a indwelled on the common bile duct side rotates and the direction of the distal end side region 201a is corrected to a desired state.

As described above, in Step S8, the stylet 5 moves toward the proximal end side while rotating, and at the same time, the needle tube 4 moves toward the proximal end side without rotating. By this manipulation, since the stylet proximal end member 54 having the stylet 5 connected thereto receives, from the first cam tube 61, a vector in the direction of the proximal end side, the stylet 5 and the needle tube 4 are pulled back toward the proximal end side. At this time, in a state in which the distal end opening portion 32 of the sheath 3 comes into contact with the target tissue, the distal end side region 201a of the tissue-fastening tool 2 indwelled on the common bile duct side acts as an anchor and the tissue-fastening tool 2 simultaneously receives a pulling force in the distal end direction. When a force by which the stylet 5 is pulled toward the proximal end side becomes stronger, there is a concern concerning a force by which the target tissue is sandwiched between the tissue-fastening tool 2 and the sheath 3 increasing and the tissue compressed with an excessive load.

In the indwelling device 1 according to this embodiment, in order to prevent an excessive load to the target tissue, when the force by which the target tissue is sandwiched between the tissue-fastening tool 2 and the sheath 3 becomes stronger, the synchronization of the stylet 5 with the movement of the needle slider 64 moving in the proximal end direction while rotating right is released and the force by which the target tissue is sandwiched between the tissue-fastening tool 2 and the sheath 3 is relieved. As described above, the first guide passage 612 imparts a vector force to the first engaging pin 55 of the stylet 5 in the direction of the proximal end side. However, when a force in the distal end direction from the tissue-fastening tool 2 becomes stronger than the vector force, the synchronization between the stylet 5 and the needle slider 64 is released, only the needle tube 4 moves toward the proximal end side, and the first engaging pins 55 moves in the distal end direction along the first guide passage 612. At this time, since the stylet 5 relatively moves to the distal end side with respect to the needle slider 64, the load can be weakened. As a result, if the force in the distal end direction from the tissue-fastening tool 2 is lower than the vector force in the proximal end direction, the stylet 5 enters a state of following the movement of the needle slider 64 again. Thus, it is possible to prevent damage to the tissue of the treatment target site. A motion of automatically adjusting the load can be achieved by suitably setting the lead angle of the first guide passage 612. To be specific, the motion can be achieved by setting the lead angle with a range of 20 degrees to 75 degrees.

When the lead angle of the first guide passage 612 is smaller than 20 degrees, since the vector force in the direction of the proximal end side imparted to the first engaging pins 55 becomes stronger, forces are first balanced when the force in the distal end direction from the tissue-fastening tool 2 becomes very strong. Thus, the sandwiched tissue is likely to be damaged. When the lead angle of the first guide passage 612 is larger than 75 degrees, since the vector force in the direction of the proximal end side imparted to the first engaging pins 55 becomes weaker, the forces are balanced in a state in which the force in the distal end direction from the tissue-fastening tool 2 is very weak. Thus, the stylet 5 is likely to be unable to be sufficiently pulled toward the proximal end side. Furthermore, it is more desirable that the lead angle be in a range of 40 degrees or more. This is because the larger the lead angle is, the smaller the diameter of the first cam tube 61 can be set. By reducing the diameter of the first cam tube 61, it is possible to reduce the diameter and weight of the main manipulation part 6.

In Step S8, when the locking pin 684c moves to the proximal end of the helical groove 622, the needle slider 64 is not rotated. Thus, the operator can perceive that the needle tube 4 is removed from the tissue. It should be noted that, as described above, due to the needle anti-movement mechanism that prevents the needle slider 64 from being advanced while being rotated again, the needle slider 64 can be neither advanced nor retracted while being rotated.

Figure 26:
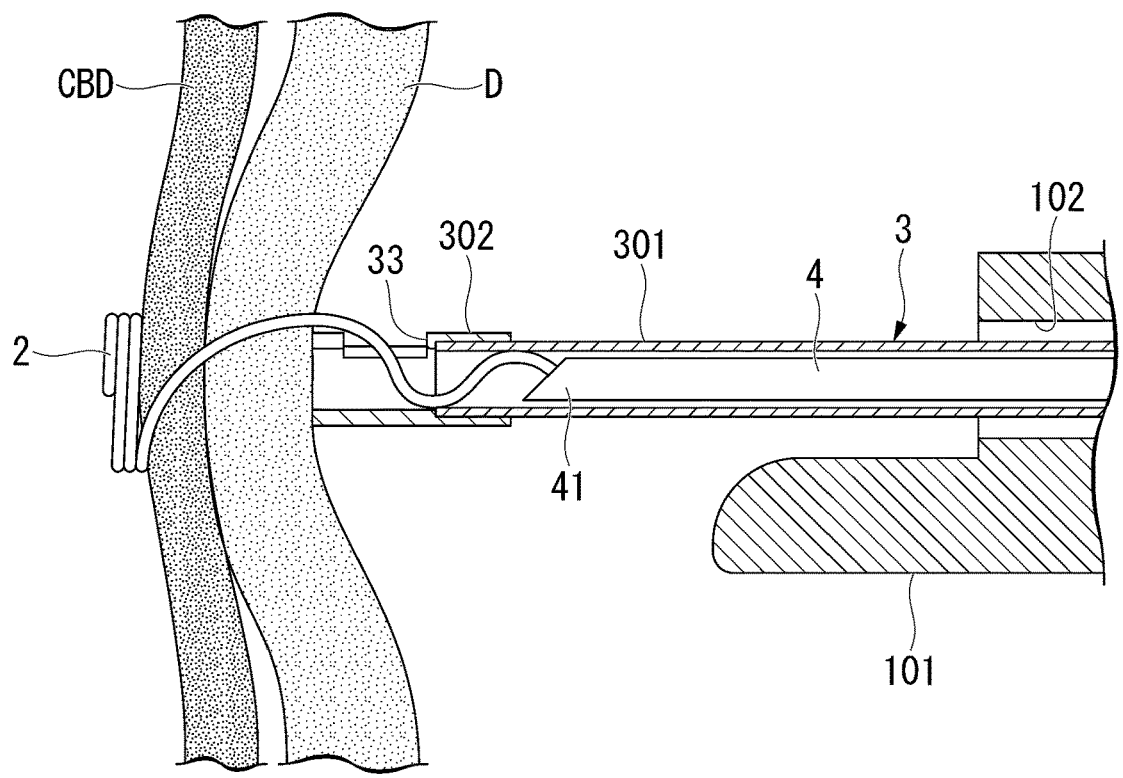
FIG. 26 is a side view showing the usage mode of the tissue-fastening tool indwelling device according to the embodiment.
Figure 27:
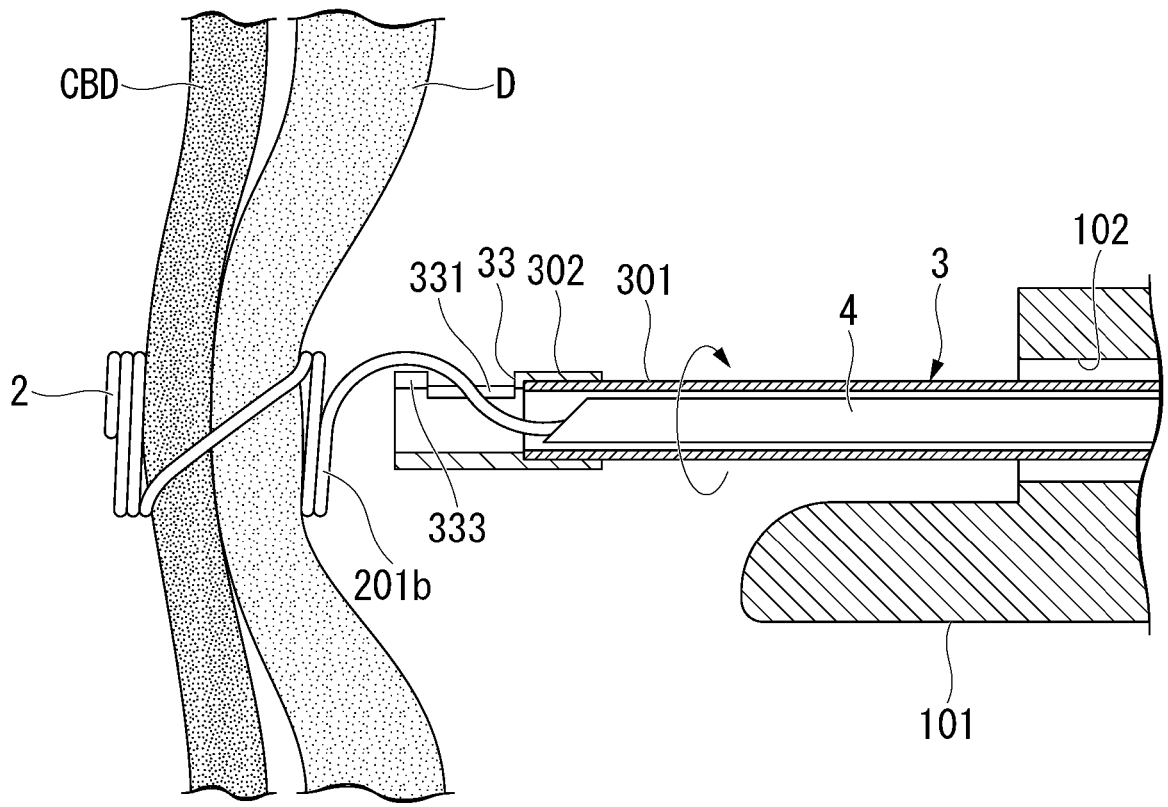
FIG. 27 is a side view showing the usage mode of the tissue-fastening tool indwelling device according to the embodiment.

Subsequently, as shown in FIG. 26, the sheath 3, the needle tube 4, and the stylet 5 are advanced by a predetermined distance (Step S9). In a state in which the distal end portion of the sheath 3 comes into contact with the duodenal tissue D, the operator loosens the fixing knob 634 and advances the fixing knob 634 until the fixing knob 634 comes into contact with the distal end of the second slit 633. Thus, the main manipulation part main body 62 comes into contact with the distal end of the sheath slider 63. By this manipulation, the distal end portion of the sheath 3 protrudes from the distal end of the treatment tool channel 102.

Since the mounting part 69 is fixed to the endoscope 100, the sheath 3 is extruded from the distal end of the endoscope insertion part 101 and the endoscope insertion part 101 relatively retracts and the distal end thereof is separated from the duodenal tissue D. In the subsequent treatment, a surgical field is imaged by an optical imaging device (not shown) provided at the distal end of the endoscope insertion part 101. The operator performs the treatment while checking the endoscopic image.

In Step S9, a force in a direction in which the main manipulation part main body 62 retracts toward the proximal end side is generated in the main manipulation part main body 62. However, since the screw part 634a of the fixing knob 634 is pressed by the resin spring 635 of the sheath slider 63, it is possible to prevent the main manipulation part main body 62 from retracting.

Since the main manipulation part main body 62 can no longer advance when the main manipulation part main body 62 comes into contact with the sheath slider 63, the operator can perceive that the main manipulation part main body 62 has been pushed to a predetermined position. Furthermore, since the main manipulation part main body 62 does not unintentionally move toward the proximal end side due to the function of the resin spring 635 even if the fixing knob 634 is not tightened, the position of the main manipulation part main body 62 does not deviate from the predetermined position.

The process of the next Step S10 is performed by the assistant and the operator cooperating. Manipulations in Step S11 and steps subsequent to Step S11 are performed when the assistant manipulates the auxiliary manipulation part 7. That is to say, the manipulation of sending the coil of the tissue-fastening tool 2 on the duodenum side is performed by the auxiliary manipulation part 7.

The auxiliary manipulation part 7 is connected to the main manipulation part 6 (Step S10). The assistant holds the auxiliary manipulation part 7 and inserts the proximal end of the Luer joint 57 of the main manipulation part 6 into a distal end opening of the sixth insertion passage 711 of the manipulation coupling part 71. When the operator or the assistant rotates the manipulation coupling part 71, the screw groove 712 of the sixth insertion passage 711 and the flange 574 formed at the proximal end portion of the Luer joint 57 are screwed together and the main manipulation part 6 and the auxiliary manipulation part 7 are connected to each other. When the rotation handle 74 is rotated right, the rotation handle 74 advances while rotating along the second guide passage 731 formed in the second cam tube 73. Since the transmission member 8 is fixed to the rotation handle 74 via the fixing member 744, the transmission member 8 advances while rotating right. Since the stylet engagement part 82 of the transmission member 8 advances while rotating, the stylet engagement part 82 comes into contact with the proximal end engagement part 56 of the stylet 5 in a short time. As shown in FIG. 9, the proximal end portion 56a has a shape that protrudes toward the proximal end side on the central axis L. For this reason, in a state in which the stylet engagement part 82 of the transmission member 8 and the proximal end of the proximal end engagement part 56 of the stylet 5 come into contact with each other, the transmission member 8 advances while rotating. Thus, the proximal end engagement part 56 of the main manipulation part 6 is fitted and engaged between two arms 82b of the stylet engagement part 82 in time. Thereafter, the rotation and advancement driving of the transmission member 8 can be transmitted to the stylet 5.

It should be noted that, as shown in FIG. 20, since the main manipulation part 6 and the auxiliary manipulation part 7 are coupled to each other by a flexible part including the cable tube 81 and the transmission member 8, adaptability can be given to a positional relationship between the main manipulation part 6 and the auxiliary manipulation part 7. Thus, the assistant can perform the manipulation without disturbing the operator while standing at a location where it is easy to operate the auxiliary manipulation part 7. Furthermore, since there is the flexible part between the main manipulation part 6 and the auxiliary manipulation part 7, the main manipulation part 6 is not strongly pushed even if the assistant strongly pushes the auxiliary manipulation part 7 in the distal end direction of the central axis L.

Also, as described above, as shown in FIGS. 14 and 16, the fitting hole 733, into which the rod-like member 734 is insertable, is exposed when the rotation handle 74 is moved to the extreme proximal end side. For this reason, the rod-like member 734 is fitted into the fitting hole 733 formed in the second cam tube 73, and thereby the rod-like member 734 is allowed to protrude outward in the radial direction of the second cam tube 73. Therefore, the rod-like member 734 is merely fitted into the fitting hole 733, and thereby the rotation handle 74 of the auxiliary manipulation part 7 can be prevented from being rotated unintentionally.

Furthermore, in a state in which the needle tube 4 is removed from two luminal tissues, i.e., the duodenal tissue D and the common bile duct tissue CBD, the needle slider 64 is prevented from being advanced again by the aforementioned needle anti-movement mechanism. Therefore, for example, when the assistant manipulates the auxiliary manipulation part 7, the needle tube 4 is prevented from being pushed out to the distal end side unintentionally.

Subsequently, the tissue-fastening tool 2 is indwelled closer to the proximal side than the duodenal tissue D (Step S11). When the assistant rotates the rotation handle 74 right, the transmission member 8 advances while rotating right.

To be specific, as shown in FIG. 15A, when the rotation handle 74 is rotationally manipulated, the second engaging pin 743 moves along the inside of the second guide passage 731 and the rotation handle 74 relatively moves to the distal end side with respect to the second cam tube 73 and approaches the auxiliary manipulation part main body 72. Furthermore, when the rotation handle 74 is rotationally manipulated, the distal end portion of the rotation handle 74 enters the gap S between the second cam tube 73 and the auxiliary manipulation part main body 72 in the first region 721a of the seventh insertion passage 721.

As described above, when the rotation handle 74 is rotationally manipulated, the transmission member 8 is configured to advance while rotating with respect to the auxiliary manipulation part 7 and to protrude from the manipulation coupling part 71. As a result, a helical movement (a helical input) of the transmission member 8 is transmitted to the stylet 5. Then, the first engaging pins 55 are separated from the distal end face of the Luer joint 57. Furthermore, since the rotation handle 74 rotates the stylet 5 while advancing the stylet 5 with respect to the Luer joint 57, the first engaging pins 55 are rotated while engaged with the slit surface of the guide slit 673 in the rotational direction of the stylet 5. At the same time, the first engaging pins 55 slide along the first guide passage 612 of the first cam tube 61. Thus, the proximal end side region 201b of the tissue-fastening tool 2 is advanced while being rotated and can be sent from the distal end of the needle tube 4 into the duodenum.

The helical pitch P1 of the first guide passage 612 of the first cam tube 61 is equal to the helical pitch P2 of the second guide passage 731 of the second cam tube 73. Furthermore, rotational directions of the first guide passage 612 and the second guide passage 731 are the same in that the rotational directions of the first guide passage 612 and the second guide passage 731 are a right direction. In the indwelling device 1, the main manipulation part 6 and the auxiliary manipulation part 7 are provided as separate bodies and the manipulation of the auxiliary manipulation part 7 is transmitted to the main manipulation part 6 via the transmission member 8. Furthermore, in consideration of manipulation properties when the main manipulation part 6 and the auxiliary manipulation part 7 are manipulated by different persons, the transmission member 8 has flexibility and has a long length in some cases. In such cases, a deviation occurs between the movement of the rotation handle 74 and the movement of the stylet engagement part 82 due to an influence of bending and a length of the transmission member 8 in a transmission path of a driving force so that movement is likely not to be accurately transmitted to the stylet 5.

However, in the indwelling device 1 according to this embodiment, since the first guide passage 612 and the second guide passage 731 are formed at the same helical pitch and in the same rotational direction, a rotational motion transmitted from the transmission member 8 can be adjusted to be the same rotational movement amount as the movement of the rotation handle 74 in the first guide passage 612. For this reason, an input in a helical direction generated by the rotational manipulation of the auxiliary manipulation part 7 is accurately output from the stylet 5 as a helical motion.

From the above, when the rotation handle 74 is rotationally manipulated, since the first engaging pins 55 of the stylet 5 rotates the needle guide 67 and the needle guide 67 rotates the sheath guide 623 as described above, the stylet 5 advances and the sheath 3 rotates in synchronization with the rotation of the stylet 5.

In Step S11 described above, as shown in FIG. 27, the tissue-fastening tool 2 enters the slit 33 of the sheath 3. The tissue-fastening tool 2 is sent from the needle tube 4 while being rotated by the sheath 3 and the stylet 5. In order to reliably transmit the rotation of the sheath 3 to the metal element wire of the proximal end side region 201b and cause the tissue-fastening tool 2 to be restored to have a correct indwelling shape, it is necessary to deliver the metal element wire while being rotated in a direction in which the metal element wire is away from the central axis L. For this reason, it is necessary for the metal element wire to not be detached from the slit 33.

If the tissue-fastening tool 2 is detached from the slit 33, the proximal end side region 201b is delivered along the central axis L and sent toward the bile duct side as it is. In this case, the tissue-fastening tool 2 is not restored to the correct indwelling shape.

In the indwelling system according to this embodiment, since the tissue-fastening tool 2 is configured not to be detached from the slit 33 of the sheath 3, the metal element wire of the proximal end side region 201b is capable of being reliably restored to the indwelling shape on the duodenum side regardless of the user's skill.

Figure 31:
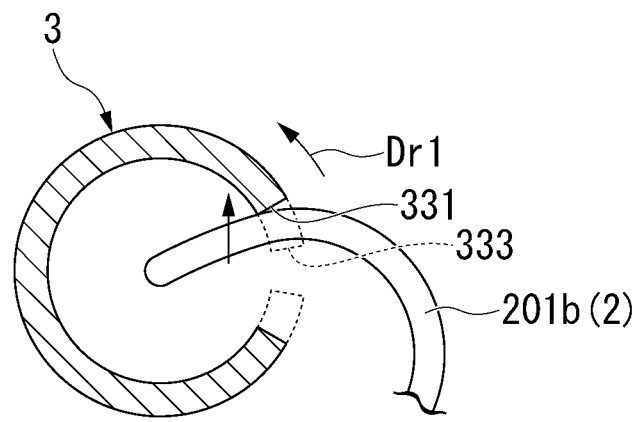
FIG. 31 is a diagram showing a behavior of a tissue-fastening tool delivered from a sheath.

The helical pitch Pin the helical shape of the first guide passage 612 is set such that the sheath 3 rotates less than one turn while the metal element wire of the proximal end side region 201b indwelled in the luminal organ on the proximal side in the coil region 201 of the tissue-fastening tool 2 is being delivered for one turn. For this reason, the delivered metal element wire is biased to have a circular arc having a diameter larger than the diameter of the helical proximal end side region 201b of the first guide passage 612 in the indwelling shape (hereinafter, this phenomenon refers to the expression "unrolled"). Since the unrolled metal element wire is biased to form a large-diameter circular arc, the unrolled metal element wire tend to move away from the central axis L, and as shown in FIG. 31, the first circumferential edge 331 is pushed to come into contact with the first circumferential edge 331 located on the downstream side in the rotational direction Dr1 of the sheath 3. When a force pushing the first circumferential edge 331 becomes stronger, there is a concern concerning the rotation of the sheath 3 which is not transmitted due to the biased metal element wire deviating to the outside of the slit 33, but the protrusion 333 is provided on the distal end side of the first circumferential edge 331 and thus the deviation of the biased metal element wire from the slit 33 is prevented.

The proximal end side region 201b is deployed from the distal end side of the central axis L toward the proximal end side thereof and indwelled, but when the coupling part 202 and the outer circumferential loop 203 are sent from the sheath 3 and restored to the indwelling shape, unlike the proximal end side region 201b, the coupling part 202 and the outer circumferential loop 203 are deployed from the proximal end side of the central axis L toward the distal end side thereof. For this reason, in the coupling part 202, and the outer circumferential loop 203, the behavior at the time of shape restoration of the tissue-fastening tool 2 changes compared with that of the proximal end side region 201b. Depending on a mode of change, the metal element wire is likely to deviate from the slit 33, or the coupling part 202 and the outer circumferential loop 203 are tangled, thereby the tissue-fastening tool 2 is likely not to be restored to the indwelling shape.

In the indwelling system according to this embodiment, by focusing on the aforementioned behavior, the helical shape of the first guide passage 612 is set such that the sheath 3 rotates one turn or more while the metal element wire constituting the coupling part 202 and the outer circumferential loop 203 is being delivered for one turn. As a result, the metal element wire sent from the sheath 3 is biased to have a circular arc having a radius of curvature smaller than radii of curvature of the coupling part 202 and the outer circumferential loop 203 in the indwelling shape (hereinafter, this phenomenon refers to the expression "rolled-tightened").

Figure 32:
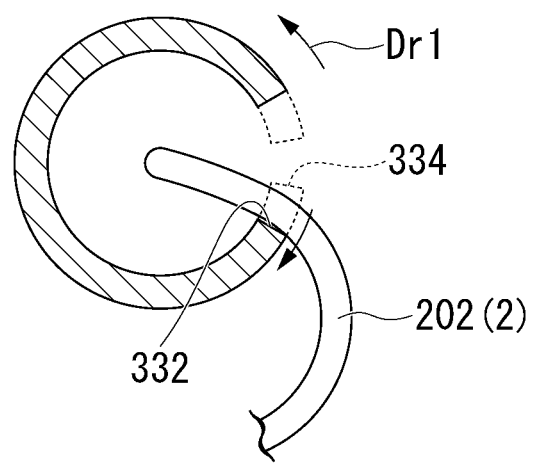
FIG. 32 is a diagram showing the behavior of the tissue-fastening tool delivered from the sheath.

When the metal element wire is rolled-tightened, a spring force of the coupling part 202 and the outer circumferential loop 203 strengthens. For this reason, the coupling part 202 and the outer circumferential loop 203 are not easily deformed so that a change in behavior at the time of shape restoration is reduced and thus the aforementioned occurrence of failure is suitably minimized. Since the rolled-tightened metal element wire is biased to form a circular arc having a smaller radius of curvature, the rolled-tightened metal element wire approaches the central axis L, and as shown in FIG. 32, the rolled-tightened metal element wire comes into contact with the second circumferential edge 332 located on the upstream side in the rotational direction Dr1 of the sheath 3 to push the second circumferential edge 332. When a force pushing the second circumferential edge 332 becomes stronger, there is a concern concerning the rotation of the sheath 3 which is not transmitted due to the biased metal element wire deviating to the outside of the slit 33, but the second protrusion 334 is provided on the distal end side of the second circumferential edge 332 and thus the deviation of the biased metal element wire from the slit 33 is prevented.

It should be noted that FIGS. 31 and 32 show a cross section of the tubular member 302 at a portion at which the first circumferential edge 331 and the second circumferential edge 332 are provided when viewed from the distal end side of the sheath 3.

The amount of turn of the sheath 3 for achieving the aforementioned effects can be set as appropriate. For example, an amount of turn of the sheath 3 until the metal element wire is delivered from the sheath 3 by a length of one turn of the proximal end side region 201b is preferably 0.5 turns or more and 0.9 turns or less. For example, an amount of turn of the sheath 3 while the metal element wire constituting the coupling part 202 is being delivered for one turn is preferably more than 1 turn and 1.8 turns or less. The amount of turn of the sheath 3 is determined solely in accordance with the helical shape of the first guide passage 612. In addition, by suitably setting the length of one winding of the proximal end side region 201b and the length of one turn of the metal element wire constituting the coupling part 202, it is possible to realize both relationships in the first guide passage having a single helical pitch.

Also, the amounts of protrusion of the protrusion 333 and the second protrusion 334 is a half or more of the diameter of the metal element wire constituting the tissue-fastening tool 2 is desirable, because the deviation of the metal element wire to the outside of the slit 33 can be suitably prevented.

It should be noted that, in the motion as an example described above, the needle tube 4 does not rotate as described above. When the one of the first engaging pins 55 of the stylet 5 on the extreme distal end side comes into contact with the distal end of the first guide passage 612 of the first cam tube 61, the advancement of the stylet 5 is completed. At this time, the distal end of the stylet 5 is exposed to the outside of the needle tube 4. Thus, the engagement between the implant-coupling part 22 of the tissue-fastening tool 2 and the distal end engagement part 51 of the stylet 5 is released and the indwelling of the tissue-fastening tool 2 is completed. In this way, the indwelling device 1 is configured such that the distal end of the stylet 5 is exposed from the distal end of the needle tube 4 when both of the main manipulation part 6 and the auxiliary manipulation part 7 perform the motion (the first motion) in which the tissue-fastening tool 2 is discharged from the distal end of the needle tube 4 by the stylet 5 being advanced with respect to the needle tube 4.

According to this embodiment, after the needle tube 4 is removed from the tissue and stored in the sheath 3, coil indwelling on the duodenum side is performed by the auxiliary manipulation part 7. That is to say, it is possible to separately perform a plurality of manipulations of the main manipulation part 6 and the auxiliary manipulation part 7 to indwell the tissue-fastening tool 2 in the treatment target tissue. Thus, the main manipulation part 6 can be reduced in size in comparison to a conventional implant-indwelling device. Therefore, it is possible to improve manipulation properties of the operator.

Furthermore, the manipulation related to the advancement and retraction of the needle tube 4 can be performed only by the main manipulation part 6 and the manipulation caused by the auxiliary manipulation part 7 is performed in a state in which the puncturing part 42 of the needle tube 4 is stored in the sheath 3. When the coil of the tissue-fastening tool 2 is indwelled on the duodenum side, the locking pin 684c passes over the oblique portion 622a and is fitted into the dent portion 622b. In this state, as long as the operator does not press the button main body 682 inward in the radial direction to be pushed in until the button main body 682 comes into contact with the base body 681, the state in which the locking pin 684c is fitted into the dent portion 622b is maintained. For this reason, as long as the operator does not intentionally press the button main body 682 inward in the radial direction, the needle slider 64 can be neither advanced nor retracted. Thus, the operator easily controls the movement of the needle tube 4. In addition, the needle tube 4 (the puncturing part 42) does not move unintentionally caused by being affected a manipulation of the assistant. For this reason, the puncturing part 42 does not damage the tissue.

According to this embodiment, the first helical mechanism is provided in the main manipulation part and the second helical mechanism is provided in the auxiliary manipulation part. Therefore, it is possible to output a manipulation that is input to the auxiliary manipulation part to the manipulation transmission member as a motion of the second helical mechanism in a predetermined helical direction. In addition, a motion which is input from the manipulation transmission member to the main manipulation part is once adjusted due to passing through the first helical mechanism and is output as a motion in the predetermined helical direction from the stylet. Therefore, even if there is an error in an input motion input to the auxiliary manipulation part and an output motion output from the auxiliary manipulation part caused by a long drive transmission path between the main manipulation part and the auxiliary manipulation part, it is possible to adjust the error by the first helical mechanism again. Therefore, a helical motion which is input to the auxiliary manipulation part is transmitted to the tissue-fastening tool via the main manipulation part with high accuracy.

According to this embodiment, since the lead angle of the first guide passage is set in a range of 20 degrees or more and 75 degrees or less, when a force sandwiching a target tissue between the tissue-fastening tool and the sheath becomes stronger, synchronization between the retraction of the needle tube and the retraction of the stylet is released. Therefore, it is possible to prevent an excessive load from being applied to the target tissue when removing the needle tube. More preferably, the lead angle is set in a range of 40 degrees or more. Since this enables a decrease in the diameter of the first cam tube, it is possible to reduce the diameter and weight of the main manipulation part.

According to this embodiment, since the state in which the tissue-fastening tool protrudes from the distal end of the needle tube and packed is the initial state, the state in which the tissue-fastening tool is stretched in the needle tube for a long period of time is not maintained and the fastening force of the tissue-fastening tool can be maintained in a suitable state.

Furthermore, the tissue-fastening tool in the packing state can be easily loaded using the jig. In the indwelling device according to this embodiment, since the tissue-fastening tool is loaded using the jig, there is no need to provide the main manipulation part with a mechanism which draws the tissue-fastening tool into the needle tube and the size of the main manipulation part can be reduced.

Furthermore, since the tubular member 302 is attached to the distal end portion of the sheath 3, the inner diameter of the distal end portion is larger than that of the coil sheath part 301. Therefore, since a large space is secured at the distal end portion of the lumen 31, when a coupling portion between the tissue-fastening tool 2 and the stylet 5 moves to the distal end portion, the coupling is smoothly released. As a result, the tissue-fastening tool 2 can be smoothly indwelled.

Although this embodiment describes the constitution in which the main manipulation part 6 and the auxiliary manipulation part 7 can be separated as an example, the main manipulation part and the auxiliary manipulation part may be configured to be inseparable, for example, by integrally configuring the stylet 5 and the transmission member 8.

This embodiment describes an example in which the protruding part 51*b* is provided on the distal end engagement part 51, the recessed part 24 is provided in the implant-coupling part 22 and the stylet 5 and the tissue-fastening tool 2 are connected to each other by the protruding part 51*b* being engaged with the recessed part 24. However, a constitution in which the recessed part is provided in the distal end engagement part and the protruding part is provided in the implant engagement part may be adopted.

Although this embodiment describes an example in which the three first engaging pins 55 are provided on the stylet proximal end member 54, the number of the first engaging pins is not limited to three, and at least one first engaging pin may be provided.

Although this embodiment describes an example in which the first guide passage 612 is a hole communicating the inside of the first cam tube 61 with and the outside thereof and the second guide passage 731 is a groove having a bottom formed on the outer circumferential surface of the second cam tube 73, for example, the second guide passage may be a hole.

In the above embodiment, the example in which the Luer joint 57 and the first rotation knob 66 are screwed into the male screw 572 and the female screw 661 is given, but the screwed structure of the Luer joint 57 and the first rotation knob 66 is not limited thereto. In the above embodiment, the example in which the movement of the Luer joint 57 to the distal side is restricted by bringing the proximal end side end face of the linear groove 573 of the Luer joint 57 into contact with the proximal end side end face of the engaging projection 643*b* of the needle slider end member 643 is given, but the structure for restricting the movement of the Luer joint 57 to the distal side is not limited thereto.

Figure 28:
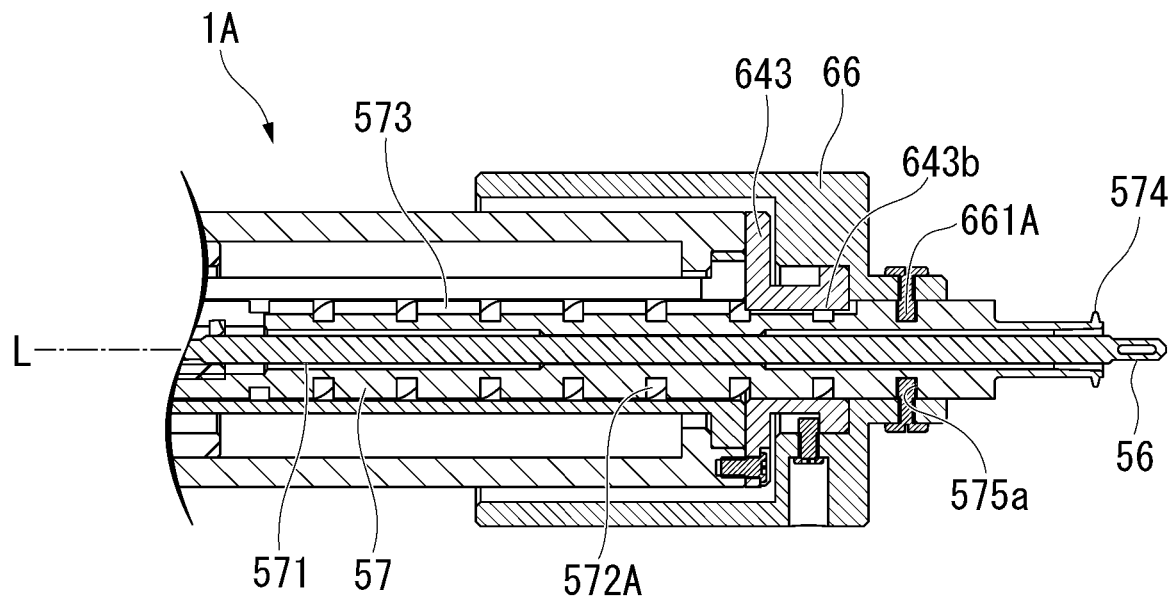
FIG. 28 is a diagram showing an example of a screwed structure of a Luer joint and the first rotation knob.

Another example of the screwed structure of the Luer joint 57 and the first rotation knob 66 is shown in FIG. 28. As shown in FIG. 28, an indwelling device 1A may be configured to be screwed into a third helical groove 572A and a projection 661A instead of the male screw 572 and the female screw 661 of the above embodiment. In this case, the third helical groove 572A is formed in an outer circumference of the Luer joint 57. That is to say, in this example, a step that extends in a helical shape is formed on the outer circumference of the Luer joint by the third helical groove 572A. The projection 661A is a sliding portion that protrudes inward from an inner circumference of the first rotation knob 66 in a radial direction and is slidable while being engaged with the step. The third helical groove 572A is configured such that the projection (the sliding portion) 661A slides along the third helical groove 572A while engaged.

In the case of this example, a proximal end face 575*a* of the third helical groove 572A is formed on the proximal end side of the Luer joint 57. That is to say, the proximal end face 575*a* is an end face provided at a terminal of the step formed by the third helical groove 572A, and the projection (the sliding portion) 661A of the first rotation knob 66 abuts this end face, and thereby functions as a restriction portion for restricting the rotation of the first rotation knob 66. In this case, the projection (the sliding portion) 661A of the first rotation knob 66 abuts the proximal end face 575*a*, and thereby the stylet 5 is restricted not to advance straight. Furthermore, in the state in which the projection (the sliding portion) 661A of the first rotation knob 66 abuts the proximal end face 575*a*, the distal end 27 of the tissue-fastening tool 2 protrudes from the needle tip of the needle tube 4, and the proximal end 21 of the tissue-fastening tool 2 is located in the needle tube 4. In this case, the proximal end side end face of the linear groove 573 of the Luer joint 57 does not come into contact with the proximal end side end face of the engaging projection 643*b* of the needle slider end member 643.

When the operator rotates the first rotation knob 66 in the right direction, the Luer joint 57 and the first cam tube 61 fixed to the Luer joint 57 move to the distal side. This movement is the same as in the above embodiment in which the male screw 572 and the female screw 661 are screwed.

In the third helical groove 572A, two helical grooves may be formed at positions that are opposite to each other in a radial direction and two projections (sliding portions) 661A that slide while being engaged with the two helical grooves may be formed.

Figure 29:
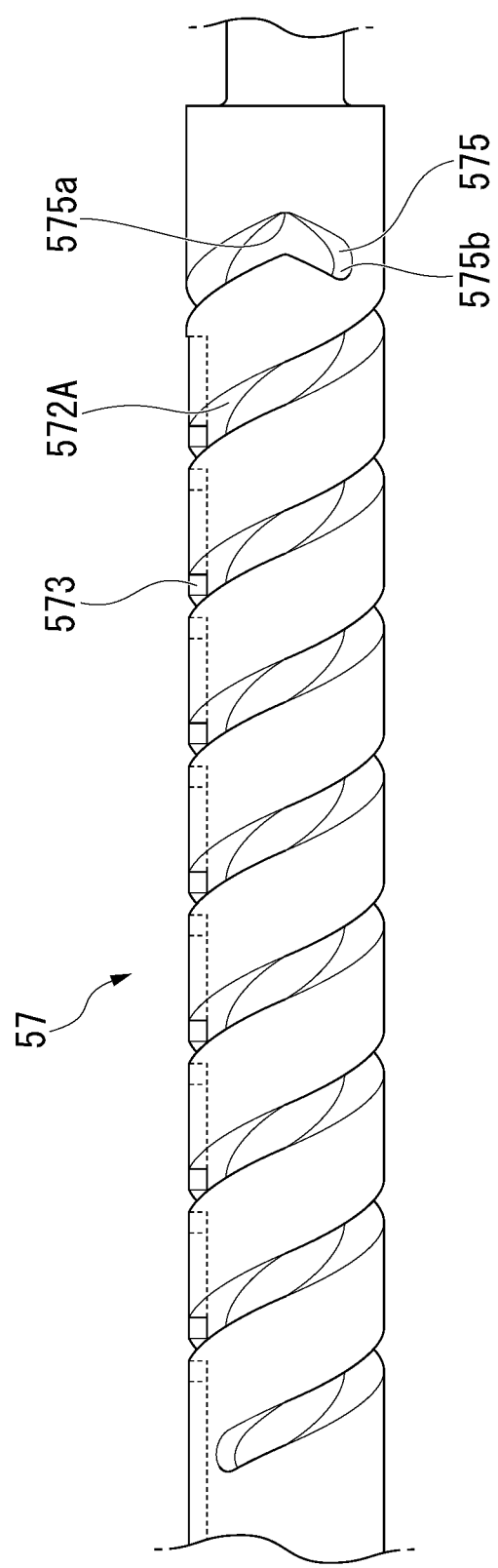
FIG. 29 is a diagram showing a proximal end portion of a third screwing groove of the Luer joint of FIG. 28.

Furthermore, in addition to the structure described in the above example, a turnback groove may be formed in a proximal end of the third helical groove 572A of the Luer joint 57. For example, as shown in FIG. 29, the turnback groove is a first turnback groove 575 at which the proximal end portion of the third helical groove 572A is turned back from the proximal end side toward the distal end side of the Luer joint 57. The first turnback groove 575 is bent such that a groove extends from the proximal end toward a distal end side of the third helical groove 572A. The first turnback groove 575 has a proximal end face (a turnback proximal end) 575*a* of the third helical groove 572A, and a turnback distal end (a first locking surface) 575*b* located closer to the distal side than the proximal end face 575*a*. A length between the proximal end face (the turnback proximal end) 575*a* and the turnback distal end 575*b* is sufficiently short over the full length of the third helical groove 572A. Accordingly, a distance in the direction of the central axis L between the proximal end face (the turnback proximal end) 575*a* and the turnback distal end 575*b* is also sufficiently short. When the first rotation knob 66 is rotated left, the Luer joint 57 moves to the distal side, and the projection 661A reaches the first turnback groove 575 in time. Then, the Luer joint 57 barely moves to the proximal side, but the projection 661A immediately comes into contact with the turnback distal end 575*b*. In this case, the first rotation knob 66 can no longer rotate left and the movement of the Luer joint 57 is also stopped.

In this example, the projection 661A enters between the turnback proximal end 575*a* and the turnback distal end 575*b* and thus the stylet 5 is in a restricted state such that the stylet 5 can be neither advanced nor retracted.

An external force in a direction along the central axis L is applied to the Luer joint 57 unintentionally in some cases. If the Luer joint 57 is pulled back to the proximal end side by the external force, the tissue-fastening tool 2 indwelled in the common bile duct is pulled back. However, the tissue-fastening tool 2 is prevented from being pulled back by an action of the first turnback groove 575. When the projection 661A is fitted into the first turnback groove 575, if an external force toward the proximal side along the central axis L is applied to the Luer joint 57, the turnback distal end 575*b* comes into contact with the projection 661A and thus the Luer joint 57 no longer moves to the proximal side. On the other hand, when an external force toward the distal end side along the central axis L is applied to the Luer joint 57, the turnback proximal end 575a comes into contact with the projection 661A and thus the Luer joint 57 no longer moves to the distal end side. That is to say, when the projection 661A is fitted into the first turnback groove 575, even if the external force in the direction of either the distal end side or the proximal end side along the central axis L is applied to the Luer joint 57, a range of the movement of the projection 661A is restricted between the turnback proximal end 575a and the turnback distal end 575b. As described above, since the distance in the direction of the central axis L between the turnback proximal end 575a and the turnback distal end 575b is sufficiently short, the Luer joint 57 is not substantially advanced or retracted by an unintended external force.

For this reason, in the case of this example, for example, in Step S7 of the above embodiment, even if the unintended external force is applied to the Luer 57 under the influence of, for instance, the manipulation of the auxiliary manipulation part 7 from the assistant, the Luer joint 57 does not substantially move due to the action of the first turnback groove 575. Therefore, the stylet 5 is restricted to allow neither the advancement nor the retraction. For this reason, the tissue-fastening tool 2 is prevented from being pulled back toward the needle tube 4 unintentionally.

Figure 30:
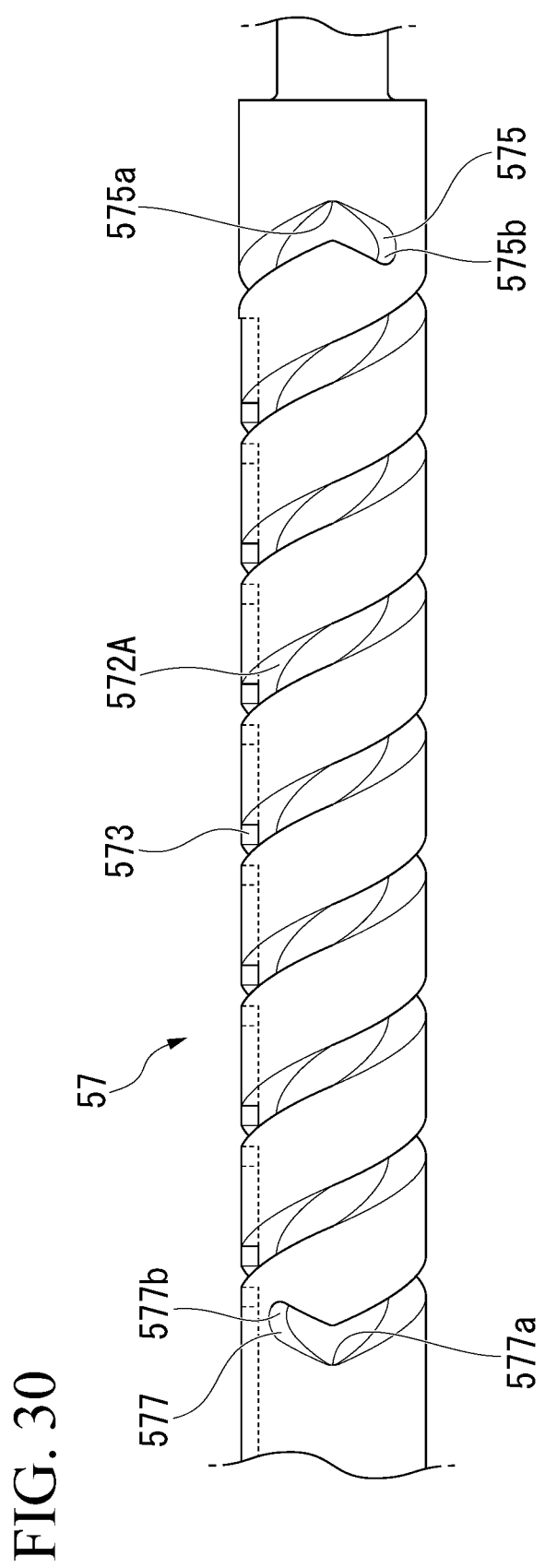
FIG. 30 is a diagram showing an example of the third screwing groove of the Luer joint of FIG. 28.

As shown in FIG. 30, the turnback groove may also be formed in the proximal end of the third helical groove 572A as well as the distal end of the third helical groove 572A. In this case, the turnback groove formed in the distal end side is referred to as a second turnback groove 577 that is bent and turned back such that a groove extends from the distal end toward the proximal end side of the third helical groove 572A. Like the first turnback groove 575, the second turnback groove 577 is bent such that the groove extends from the distal end toward the proximal end side of the third helical groove 572A, and has a distal end face (a turnback distal end) 577a of the third helical groove 572A, and a turnback proximal end (a second locking surface) 577b located at more proximal side than the distal end face. A length between the turnback proximal end 577b and the distal end face (the turnback distal end) 577a is sufficiently short over the full length of the third helical groove 572A. Therefore, the distance in the direction of the central axis L between the turnback proximal end 577b and the distal end face (the turnback distal end) 577a is also sufficiently short.

When the projection 661A is fitted into the second turnback groove 577, if an external force toward the distal side along the central axis L is applied to the Luer joint 57, the distal end face (the turnback distal end) 577a comes into contact with the projection 661A and thus the Luer joint 57 no longer moves to the distal side. On the other hand, when an external force toward the proximal side along the central axis L is applied to the Luer joint 57, the turnback proximal end 577b comes into contact with the projection 661A and thus the Luer joint 57 no longer moves to the proximal end side. That is to say, when the projection 661A is fitted into the second turnback groove 577, even if the external force in the direction of either the distal end side or the proximal end side along the central axis L is applied to the Luer joint 57, the range of the movement of the projection 661A is restricted between the turnback proximal end 577b and the distal end face (the turnback distal end) 577a. As described above, since the distance in the direction of the central axis L between the turnback proximal end 577b and the distal end face (the turnback distal end) 577a is sufficiently short, the Luer joint 57 is not substantially advanced or retracted by an unintended external force. Therefore, in the second turnback groove 577, like the first turnback groove 575, the projection 661A enters between the turnback proximal end 577b and the distal end face (the turnback distal end) 577a and thus the stylet 5 is restricted to allow neither the advancement nor the retraction.

For this reason, in the case of this example, for example, in Step S6 of the above embodiment, although the unintended external force is applied to the Luer joint 57, the Luer joint 57 does not substantially move due to the action of the second turnback groove 577. Therefore, also in this case, the stylet 5 is restricted to allow neither the advancement nor the retraction. For this reason, the tissue-fastening tool 2 is prevented from being pushed out of the needle tube 4 unintentionally.

It should be noted that, in the present example, a method of restricting the movement of the Luer joint 57 in the direction of the central axis L may be different from that of the above embodiment. As described above, the projection 661A is configured to be fitted into the third helical groove (the third helical groove) 572A, and the opposite ends 575a and 575b of the third helical groove 572A (the end portions of the turnback grooves 575 and 577 when the turnback grooves 575 and 577 are provided) and the projection 661A come into contact with each other. Thus, the rotation of the first rotation knob 66 is restricted, and the movement of the Luer joint 57 is stopped. On the other hand, in the above embodiment, the movement of the Luer joint 57 toward the distal side is restricted by contacting the proximal end side end face of the linear groove 573 of the Luer joint 57 with the proximal end side end face of the engaging projection 643b of the needle slider end member 643. In addition, the movement of the Luer joint 57 toward the proximal side is restricted by the female screw 661 reaching the distal end side terminal of the male screw 572 of the Luer joint 57 which is threadedly engaged with the female screw 661.

While the embodiments and the examples of the present disclosure have been described in detail above with reference to the drawings, the specific configuration is not limited to the embodiments and includes design changes and the like within a scope that does not depart from the gist of the present disclosure.

For example, in the above examples, the slit is formed at the distal end of the sheath by hollowing a part of the tubular member, but instead, the sheath including the slit and a protrusion may be formed by molding a resin in a shape having the slit at a distal end portion.

Furthermore, the constituent elements described in each of the embodiments and each of the examples can be constituted by appropriately combining them.

What is claimed is:

1. A tissue-fastening tool indwelling system comprising:
   a sheath extending from a distal end to a proximal end;
   a needle tube disposed in the sheath so as to be projectable and retractable from the distal end of the sheath;
   a tissue-fastening tool comprising an element wire including a coil region capable of being:
      in a stretched state inside the needle tube, and
      restored to a coil shape in which a plurality of windings have an identical winding diameter when delivered outside the needle tube;
   a stylet connected to an end portion of the tissue-fastening tool inside the needle tube; and
   a manipulation part configured to advance the stylet and rotate the sheath in a first direction around a longitudinal axis when the stylet is advanced,
   wherein:
      the sheath includes a slit at its distal end, the slit includes a proximal portion and a distal portion, the distal portion includes two protrusions, and a width between the two protrusions of the distal portion of the slit is smaller than a width of the proximal portion of the slit, and in a state in which the tissue-fastening tool is at least partially disposed inside the needle tube and a distal end of the needle tube is located at a proximal side of the distal end of the sheath:

the manipulation part is configured to operate such that the coil region of the tissue-fastening tool is deployed from the sheath by a length of one winding of the coil region per rotation of the sheath by an amount of less than one turn, and a portion of the tissue-fastening tool protruding from the sheath is biased to have a diameter larger than the winding diameter of the coil region.

2. The tissue-fastening tool indwelling system according to claim 1, wherein the manipulation part includes:

a cam tube including a guide groove formed in a wall of the cam tube, the guide groove having a helical shape at a pitch longer than the length of one winding of the coil region; and a guide part which includes a slit formed linearly along a longitudinal axis and is capable of transmitting a rotational torque to the sheath, wherein:

the stylet includes a guided part which protrudes in a radial direction from an outer circumferential surface of a proximal end region of the stylet, and is slidably fitted into the guide groove and the slit of the guide part, and the manipulation part is configured to operate such that the stylet is advanced while rotating with respect to the needle tube, and the sheath is rotated in the first direction when the guided part of the stylet moves along the guide groove and rotates the guide part while being engaged in the slit of the guide part.

3. The tissue-fastening tool indwelling system according to claim 1, wherein:

the slit has a first circumferential edge and a second circumferential edge opposite to each other in the first direction, the first circumferential edge is located on a downstream side of the second circumferential edge in the first direction, and a first protrusion of the two protrusions protrudes from the first circumferential edge towards an upstream side in the first direction, and the portion of the tissue-fastening tool protruding from the sheath is configured to contact the first circumferential edge such that deviation of the protruding portion of the tissue-fastening tool from the slit of the sheath is minimized by the first protrusion.

4. The tissue-fastening tool indwelling system according to claim 3, wherein:

the tissue-fastening tool further includes:

a coupling part which is connected to a proximal end side of the coil region and is capable of being restored to a shape that helically extends from the proximal end side of the coil region toward a distal end side of the coil region while extending outward in a radial direction from the coil region when delivered outside the needle tube; and an outer circumferential loop which is connected to a proximal end side of the coupling part and capable of being restored to a closed loop shape surrounding the coil region when deployed outside the needle tube, the second circumferential edge is located on an upstream side of the first circumferential edge in the first direction, and a second protrusion of the two protrusions protrudes from the second circumferential edge towards a downstream side in the first direction, and the manipulation part is configured to operate such that the tissue-fastening tool is advanced while being rotated, and the element wire constituting the coupling part is delivered from the sheath by a length of one turn of the coupling part per rotation of the sheath in the first direction by an amount of more than one turn, and a portion of the coupling part protruding from the sheath is biased to have a radius of curvature smaller than a radius of a helical curvature of the coupling part fully delivered from the sheath, and is configured to contact the second circumferential edge such that deviation of the protruding portion of the coupling part from the slit of the sheath is minimized by the second protrusion.

5. The tissue-fastening tool indwelling system according to claim 1, wherein:

the tissue-fastening tool further includes:

a coupling part connected to a proximal end of the element wire of the coil region, and capable of being restored to a shape that helically extends from a proximal end side of the coil region toward a distal end side of the coil region and extends outward in a radial direction from the coil region when deployed outside the needle tube, and an outer loop which is connected to a proximal end of the element wire of the coupling part, and is capable of being restored to a helical shape that is positioned outward in the radial direction from the coil region and has a helical diameter larger than the winding diameter of the coil region when deployed outside the needle tube, wherein in a state in which the tissue-fastening tool is partially disposed inside the needle tube and the distal end of the needle tube is located on the proximal side of the distal end of the sheath, the manipulation part is configured to operate such that:

the tissue-fastening tool is delivered from the sheath by a length of one winding of the coupling part and the outer loop per rotation of the sheath in the first direction by an amount of one turn or more, and the element wire of the coupling part and the outer loop delivered from the sheath is biased to form a circular arc having a diameter smaller than the helical diameter.

6. The tissue-fastening tool indwelling system according to claim 5, wherein the manipulation part includes a cam tube including a guide groove formed in a wall of the cam tube, the guide groove having a helical shape at a pitch longer than the length of one winding of the coil region; and the pitch of the guide groove is set such that the tissue-fastening tool is delivered from the sheath by a length of one turn of the coupling part and the outer loop and the sheath is rotated by a rotation amount of one turn or more.

7. The tissue-fastening tool indwelling system according to claim 6, wherein the pitch of the guide groove is set to be:

longer than the length of one winding of the coil region, and shorter than at least one of a length of one winding of the coupling part and a length of one winding of the outer loop.

8. A method for indwelling a tissue-fastening tool via a tissue-fastening tool indwelling system,
the method comprising:
operating a manipulation part to advance a stylet connected to an end portion of the tissue-fastening tool with respect to a needle tube in which the tissue-fastening tool and the stylet are disposed so as to protrude the tissue-fastening tool from a distal end of the needle tube, and indwelling a distal end side region of the tissue-fastening tool in a first luminal organ, the needle tube being projectably and retractably disposed in a sheath, where the sheath being rotated in a first direction around a longitudinal axis when the manipulation part is operated to advance the stylet, the tissue-fastening tool comprising an element wire including a coil region that is capable of being restored from a stretched state inside the needle tube to a coil shape in which a plurality of windings have an identical winding diameter when delivered outside the needle tube;
pulling the needle tube out of a wall of the first luminal organ and a wall of a second luminal organ while a distal end opening portion of the sheath is brought into contact with the wall of the second luminal organ in a state in which a distal end side region of the coil region of the tissue-fastening tool is indwelled in the first luminal organ and storing the needle tube in the sheath; and
indwelling a proximal end side region of the tissue-fastening tool in the second luminal organ by delivering the proximal end side region of the tissue-fastening tool from the sheath while biasing the proximal end side region to have a diameter larger than the winding diameter of the coil region,
wherein the sheath includes a slit at its distal end, the slit includes a proximal portion and a distal portion, the distal portion includes two protrusions, and a width between the two protrusions of the distal portion of the slit is smaller than a width of the proximal portion of the slit.

9. The method according to claim 8, wherein
the coil region is deployed from the sheath by a length of one winding of the coil region per rotation of the sheath by an amount of less than one turn.

10. The method according to claim 8, wherein:
the tissue-fastening tool further includes:
a coupling part which is connected to a proximal end of the element wire of the proximal end side region, and has a shape that helically extends from the proximal end side region toward the distal end side region of the coil region and extends outward in a radial direction from the coil region when delivered outside the needle tube, and
an outer loop which is connected to a proximal end of the element wire of the coupling part, and has a helical shape that is positioned outward in the radial direction from the coil region and has a helical diameter larger than the winding diameter of the coil region when delivered outside the needle tube,
the tissue-fastening tool is further indwelled into the second luminal organ by biasing the coupling part and the outer loop of the tissue-fastening tool so as to form a circular arc having a diameter smaller than the helical diameter after protruding the coil region from the sheath.

11. The method according to claim 10, wherein
when delivering the tissue-fastening tool from the sheath while biasing the coupling portion and the outer loop to form the circular arc having a diameter smaller than the helical diameter, the tissue-fastening tool is deployed from the sheath by a length of one winding of the coupling part and the outer loop per rotation of the sheath by an amount of one turn or more.

* * * * *